(12) United States Patent
Ung et al.

(10) Patent No.: US 8,905,988 B2
(45) Date of Patent: Dec. 9, 2014

(54) DISPOSAL BAG-SYSTEM FOR A DISPOSABLE OBJECT

(75) Inventors: Sideth Ung, Suwanee, GA (US); Armando Durazo, Jacksonville, FL (US)

(73) Assignee: Sideth Ung, Suwanee, GA (US)

( * ) Notice: Subject to any disclaimer, the term of this patent is extended or adjusted under 35 U.S.C. 154(b) by 167 days.

(21) Appl. No.: 13/312,326

(22) Filed: Dec. 6, 2011

(65) Prior Publication Data

US 2012/0226256 A1    Sep. 6, 2012

Related U.S. Application Data

(60) Provisional application No. 61/447,753, filed on Mar. 1, 2011.

(51) Int. Cl.
*A61F 13/15* (2006.01)
*A61F 13/20* (2006.01)
*A61F 13/551* (2006.01)

(52) U.S. Cl.
CPC ......... *A61F 13/5515* (2013.01); *A61F 13/5512* (2013.01)
USPC .................................................. 604/385.13

(58) Field of Classification Search
CPC ..................... A61F 13/5512; A61F 2013/8402
USPC ............. 604/385.02, 385.13, 153.01–153.14, 604/526–531
See application file for complete search history.

(56) References Cited

U.S. PATENT DOCUMENTS

| | | |
|---|---|---|
| 3,731,689 A | 5/1973 | Schaar |
| 3,865,110 A | 2/1975 | Traverse |
| 3,927,674 A | 12/1975 | Schaar |
| 4,085,753 A | 4/1978 | Gellert |
| 4,430,087 A | 2/1984 | Azpiri |
| 4,604,096 A | 8/1986 | Dean et al. |
| 4,743,240 A | 5/1988 | Powell |
| 4,808,175 A | 2/1989 | Hansen |
| 4,923,455 A | 5/1990 | Dean et al. |
| 4,964,859 A | 10/1990 | Feldman |
| 5,037,414 A | 8/1991 | Booth |
| 5,141,505 A | 8/1992 | Barrett |
| 5,304,158 A | 4/1994 | Webb |
| 5,582,605 A | 12/1996 | Lepie |

(Continued)

OTHER PUBLICATIONS

Preliminary Report on Patentability for PCT/US12/22632 dated Sep. 12, 2013.

(Continued)

*Primary Examiner* — Melanie Hand
*Assistant Examiner* — Aundria Hairell

(57) ABSTRACT

A disposal-bag system attached to or formed at least partially by a disposable object (e.g., a diaper) includes a container that houses a disposal bag folded into a compact arrangement. The container is generally thin and flat and sized for storing the bag, and the bag is sized for holding the disposable object that the system is used with. And the bag is at least partially removable from the container so that the disposable object can be placed into it for disposal. In use, the container is opened, the bag is extended from the container and opened, the disposable object is grasped by reaching through the bag, the bag is inverted to now hold the disposable object, and the bag is closed and disposed of. In this way, the disposal-bag system provides a convenient, sanitary, and self-contained method of disposing of soiled diapers or other disposable objects.

15 Claims, 29 Drawing Sheets

(56) References Cited

U.S. PATENT DOCUMENTS

| | | |
|---|---|---|
| D384,150 S | 9/1997 | Gray et al. |
| 5,702,379 A | 12/1997 | Preiss |
| 5,778,110 A | 7/1998 | Furuya |
| 6,488,222 B1 * | 12/2002 | West et al. ............... 242/160.4 |
| 6,605,071 B1 | 8/2003 | Gray et al. |
| 7,569,038 B1 | 8/2009 | Salem, Jr. |
| 7,749,209 B1 | 7/2010 | Vuckovic |
| 2002/0004656 A1 | 1/2002 | Khan et al. |
| 2002/0065500 A1 | 5/2002 | Rossi |
| 2005/0038403 A1 | 2/2005 | Singleton |
| 2005/0182379 A1 | 8/2005 | Olsen et al. |
| 2005/0256487 A1 | 11/2005 | Williams |
| 2005/0267432 A1 | 12/2005 | Sundberg et al. |
| 2006/0020252 A1 | 1/2006 | Strong |
| 2006/0282056 A1 | 12/2006 | McDonald |
| 2007/0080092 A1 * | 4/2007 | DeLuca ..................... 206/554 |
| 2008/0051744 A1 | 2/2008 | Cummings |
| 2009/0326501 A1 | 12/2009 | Foley et al. |
| 2010/0022979 A1 | 1/2010 | Carnegie et al. |
| 2010/0078456 A1 * | 4/2010 | Mottram et al. ............ 224/576 |

OTHER PUBLICATIONS

International Search Report for PCT/US12/22632 dated May 25, 2012.

* cited by examiner

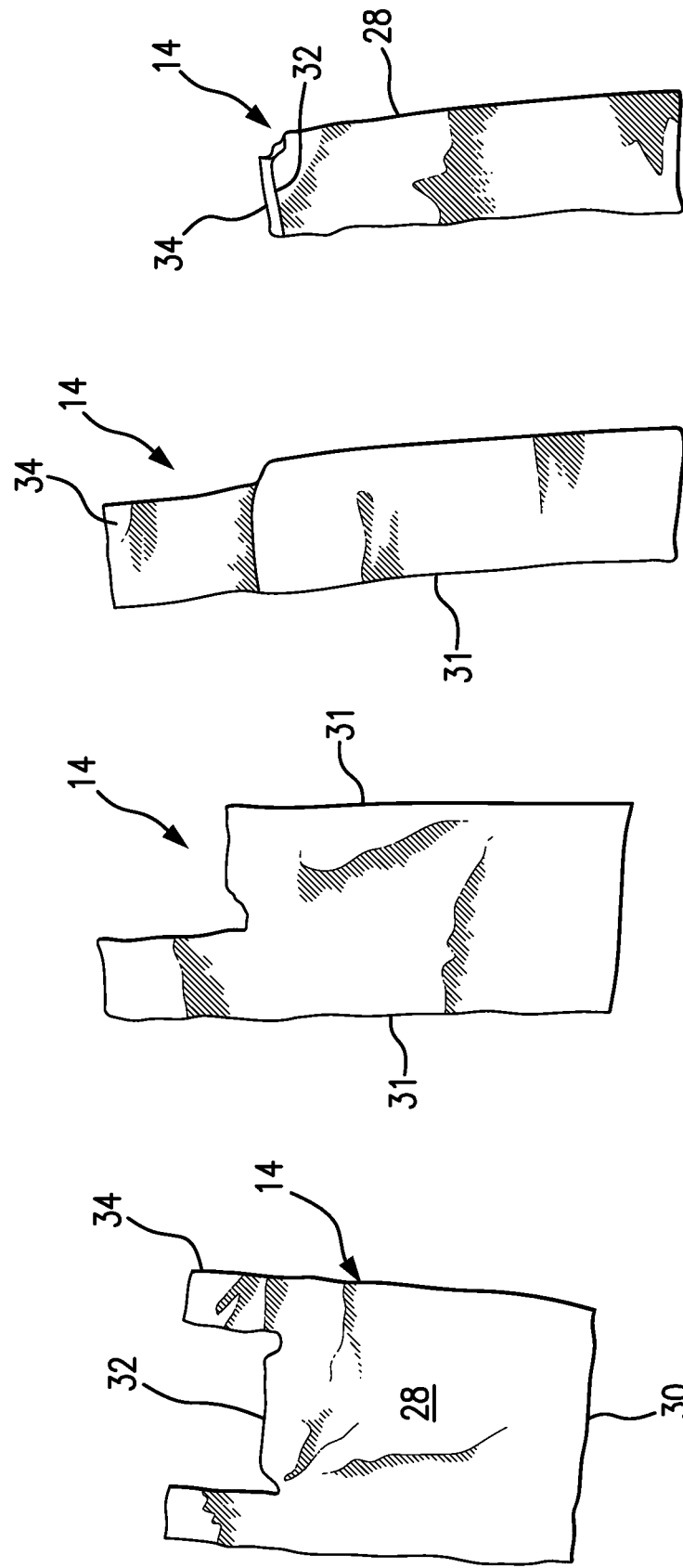

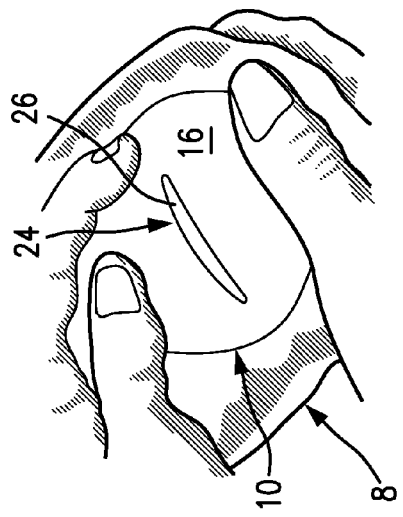
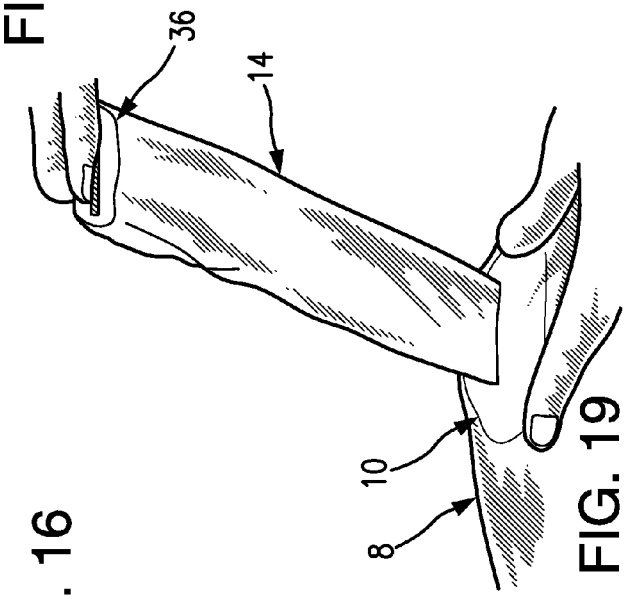
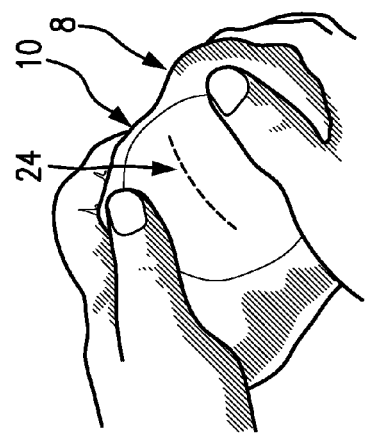
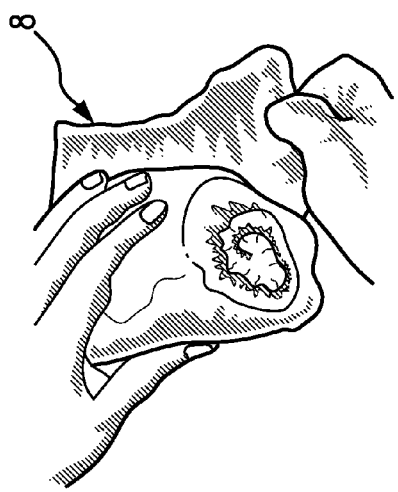
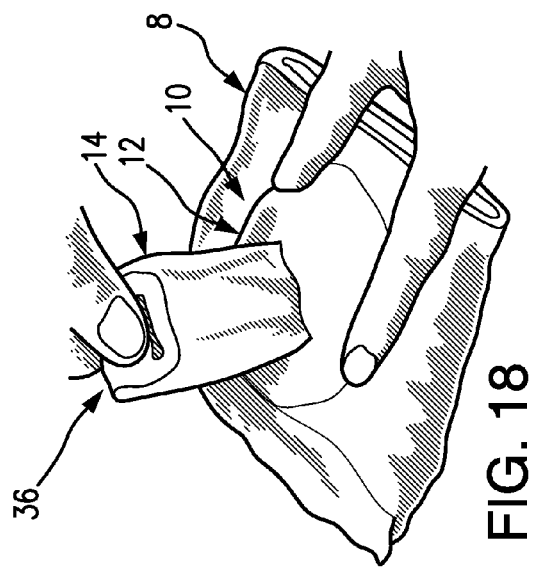

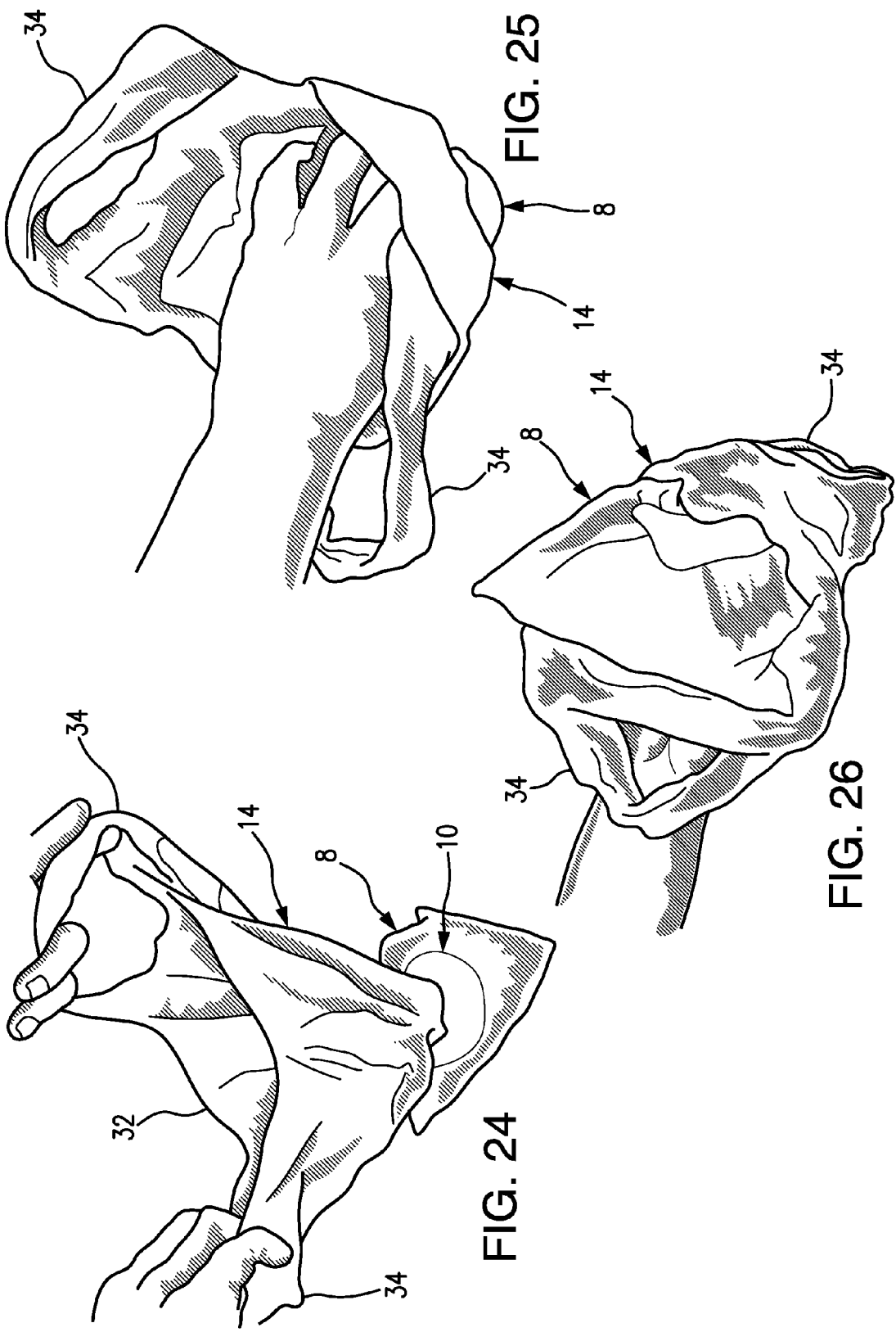

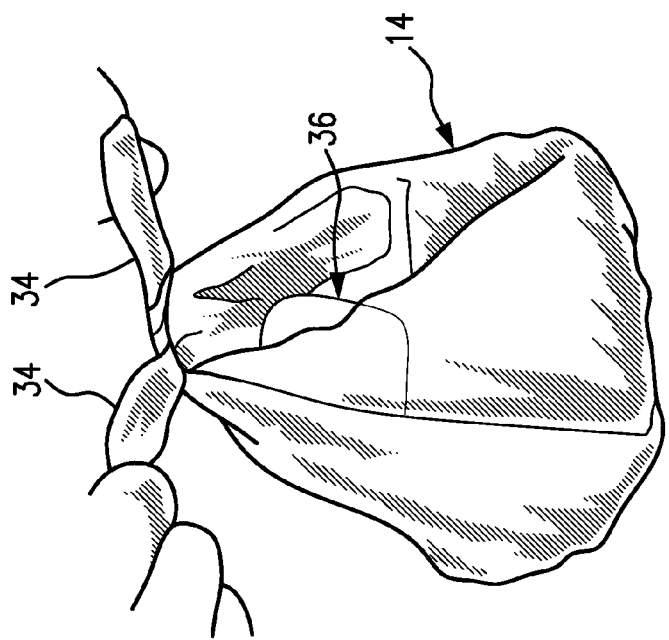
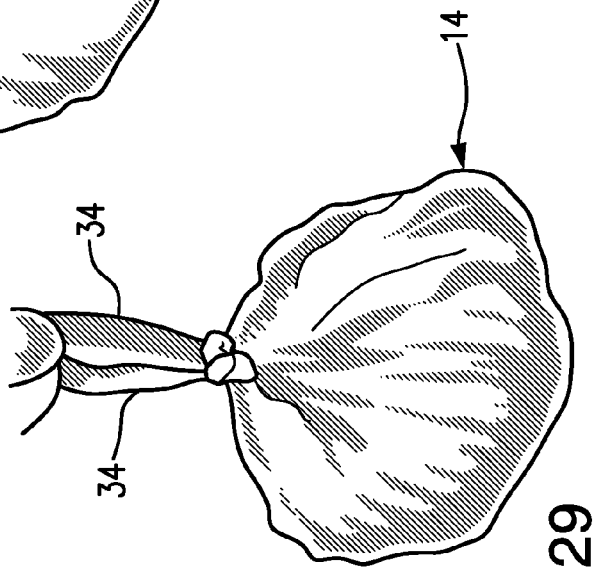
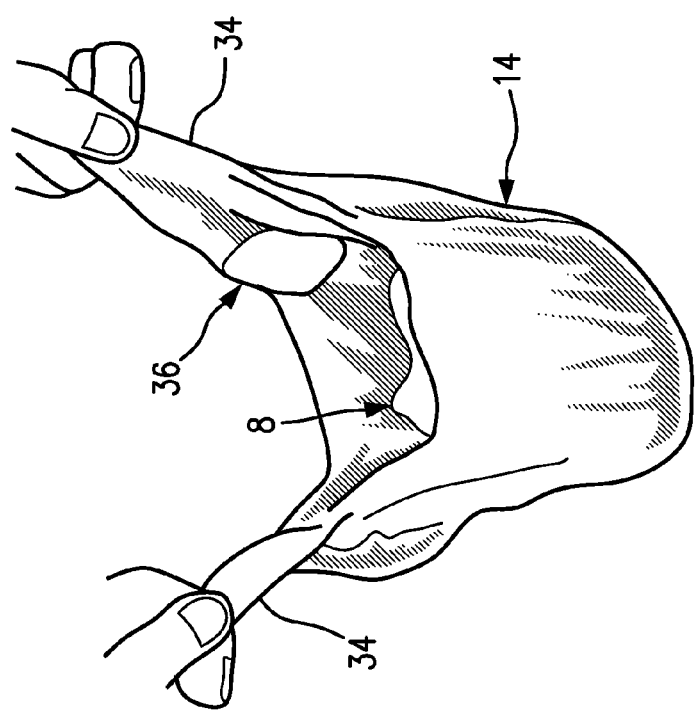
FIG. 28
FIG. 29
FIG. 27

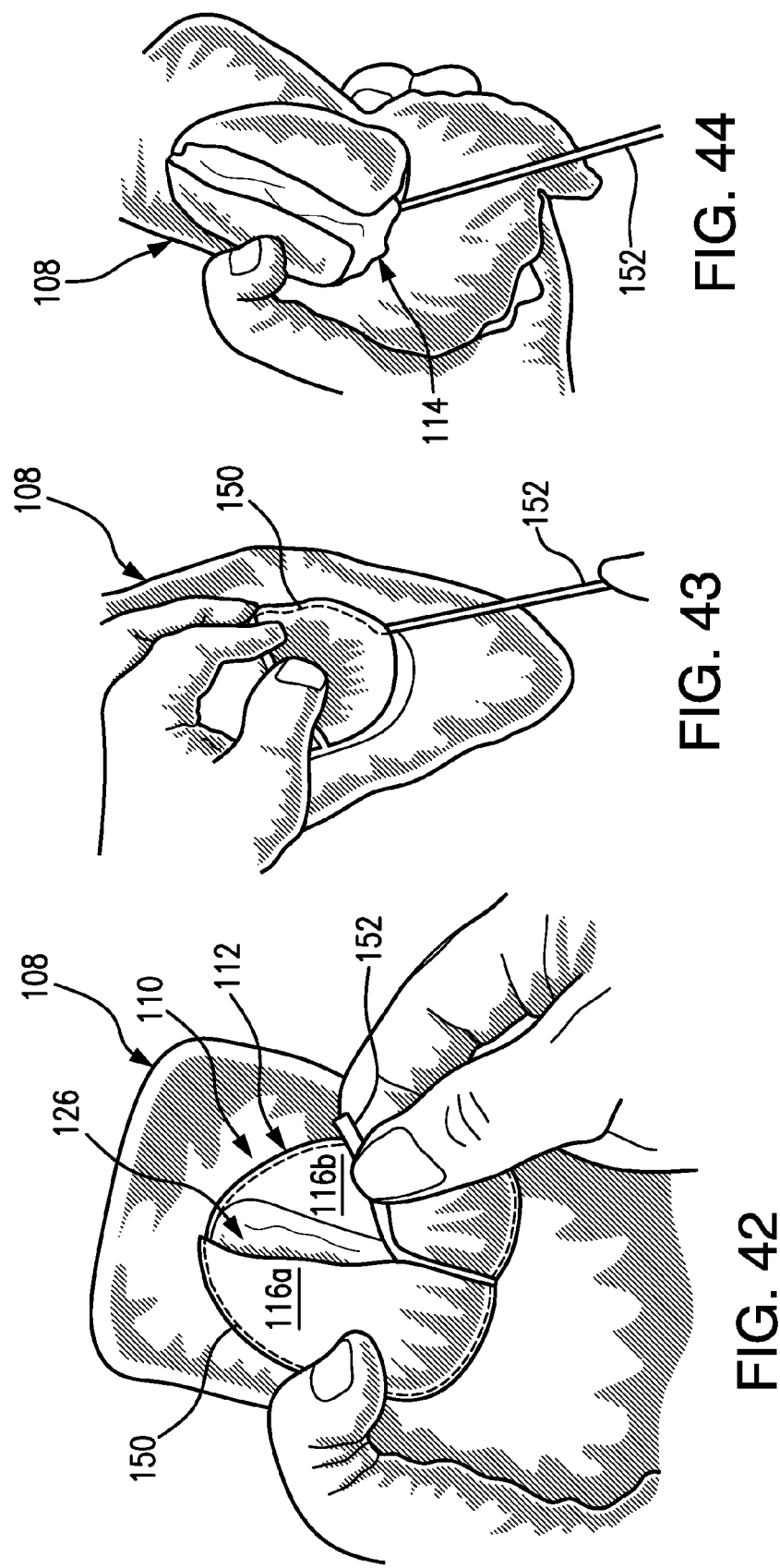

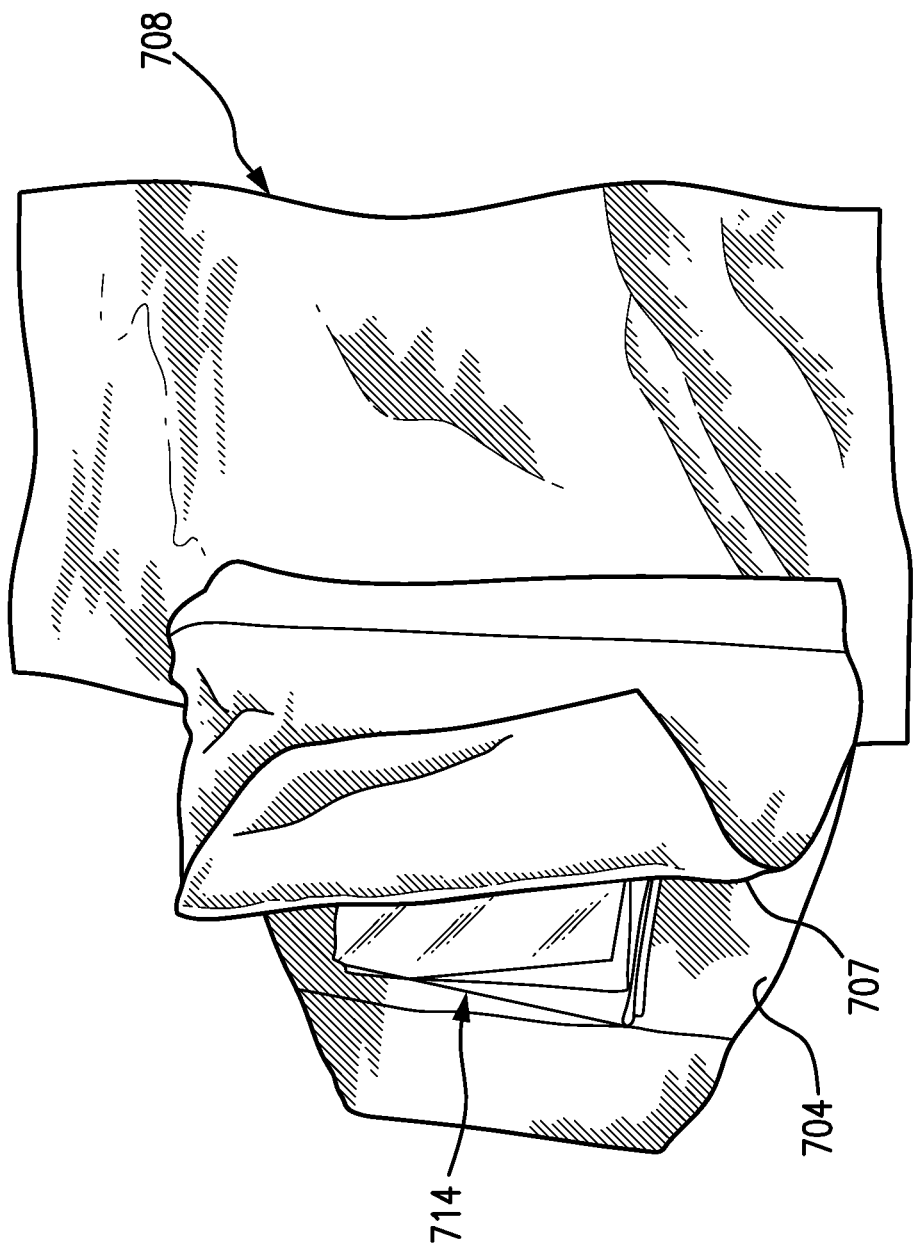

DISPOSAL BAG-SYSTEM FOR A DISPOSABLE OBJECT

CROSS-REFERENCE TO RELATED APPLICATION

This application claims the priority benefit of U.S. Provisional Patent Application Ser. No. 61/447,753, filed Mar. 1, 2011, which is hereby incorporated herein by reference.

TECHNICAL FIELD

The present invention relates generally to disposable, wearable, moisture-absorptive objects such as diapers and, in particular, to systems and methods for the disposal of such disposable objects.

BACKGROUND

Diapers for children are typically of either a reusable or a disposable type. Reusable diapers are made of a material (e.g., cotton) such that they can be washed and reused, whereas disposable diapers are made of a material (e.g., cellulose absorbent core and plastic sheeting) such that they can be cost-effectively made and disposed of after being soiled once. Disposable diapers are typically disposed of by removing them from the child and placing them in a plastic bag for disposal. Disposal of the soiled diaper can be a rather unpleasant undertaking in that it is often inconvenient to do and involves handling an unsanitary and smelly diaper full of fecal matter and urine. This is particularly problematic when a diaper change is needed in a situation in which a disposal bag is not readily available to put the soiled diaper into. To avoid this situation, caregivers typically carry around extra disposal bags (e.g., plastic grocery bags) for soiled diapers. But even when carrying around and using extra disposal bags, handling and disposing the soiled diaper still tends to be rather unpleasant, and care must be taken to always have plenty of the disposal bags on hand.

These same issues can be problematic not just for infant diapers but also for other wearable moisture-absorbent objects such as adult diapers and feminine hygiene products. And there are other situations in which unsanitary, fluid-carrying, disposable objects need to be disposed of, such as medical waste, in which safely handling the objects for disposal can be problematic.

Accordingly, it can be seen that there exists a need for a better way to provide for the disposal of disposable fluid-absorbent objects such as diapers. It is to the provision of solutions to this and other problems that the present invention is primarily directed.

SUMMARY

Generally described, the present invention relates to a disposal-bag system that is attached to or formed at least partially by a disposable object (e.g., a diaper) and includes a container (i.e., a pod) that houses a disposal bag that is folded into a compact arrangement. The container is generally thin and flat and sized for storing the bag, and the bag is sized for holding the diaper or other disposable object that the system is to be used with. And the bag is at least partially removable from the container so that the diaper or other object can be placed into it for disposal. In use, the diaper or other disposable object is rolled up, the container is opened, the bag is extended from the container and opened, the diaper is grasped by reaching through the opened bag, the bag is inverted to now hold the diaper, and the diaper-holding bag is closed and disposed of. In this way, the disposal-bag system provides a convenient, sanitary, and self-contained method of disposing of soiled diapers or other disposable objects.

The specific techniques and structures employed by the invention to improve over the drawbacks of the prior systems and methods and to accomplish the advantages described herein will become apparent from the following detailed description of example embodiments of the invention and the appended drawings and claims.

BRIEF DESCRIPTION OF THE DRAWINGS

FIG. 6 is a plan view of the disposal bag of the disposal-bag system of FIG. 2, showing the disposal bag laid flat according to a first example method of manufacturing the disposal-bag system.

FIG. 7 shows the bag of FIG. 6 folded over once.

FIG. 8 shows the bag of FIG. 7 folded over again (twice total).

FIG. 9 shows the bag of FIG. 8 with its loop handles folded in.

FIG. 15 is a perspective view of the diaper and disposal-bag system of FIG. 14, showing the diaper, now soiled, being rolled up according to a first example method of using the disposal-bag system to dispose of the diaper.

FIG. 16 shows the rolled-up diaper and disposal-bag system of FIG. 15 being held while the openable closure of the disposal-bag container is being opened.

FIG. 17 shows the rolled-up diaper and disposal-bag system of FIG. 16 with the container openable closure in an opened state forming an opening.

FIG. 18 shows the rolled-up diaper and disposal-bag system of FIG. 17 with the disposal bag being pulled to extend it from the container through the opening.

FIG. 19 shows the rolled-up diaper and disposal-bag system of FIG. 18 with the disposal bag pulled taut and with its bottom remaining bonded to the bottom sheet of the container.

FIG. 24 shows the rolled-up diaper and disposal-bag system of FIG. 23 with the bag being fully opened.

FIG. 25 shows the rolled-up diaper and disposal-bag system of FIG. 24 with the user's hand reaching into the bag to grasp the diaper.

FIG. 26 shows the rolled-up diaper and disposal-bag system of FIG. 25 with the bag being inverted inside-out.

FIG. 27 shows the rolled-up diaper and disposal-bag system of FIG. 26 with the bag inverted so that the diaper is now contained within the inside-out bag.

FIG. 28 shows the rolled-up diaper and disposal-bag system of FIG. 27 with the loop handles being tied together to close the bag.

FIG. 29 shows the rolled-up diaper and disposal-bag system of FIG. 28 with the diaper-containing bag in a tied closed state.

FIG. 38 shows the bag of FIG. 37 with its drawstring exposed portions folded in.

FIG. 42 is a perspective view of the disposal-bag system of FIG. 33, applied to a diaper, showing the diaper, now soiled, rolled up and the disposal-bag container opened while a pull-string is being pulled through the opening according to a second example method of disposing of a disposable diaper using the disposal-bag system.

FIG. 43 shows the rolled-up diaper and disposal-bag system of FIG. 42 with the pull-string being pulled to release stitching holding the two top sheet sections to the bottom sheet of the disposal-bag container.

FIG. 44 shows the rolled-up diaper and disposal-bag system of FIG. 43 with the pull-string pulled to completely separate the two top sheet sections from the bottom sheet.

FIG. 61 is a perspective view of the disposal-bag system and diaper of FIG. 60, showing the bag positioned between the outer and internal sheets of the diaper.

DETAILED DESCRIPTION OF EXAMPLE EMBODIMENTS

Figure 1:
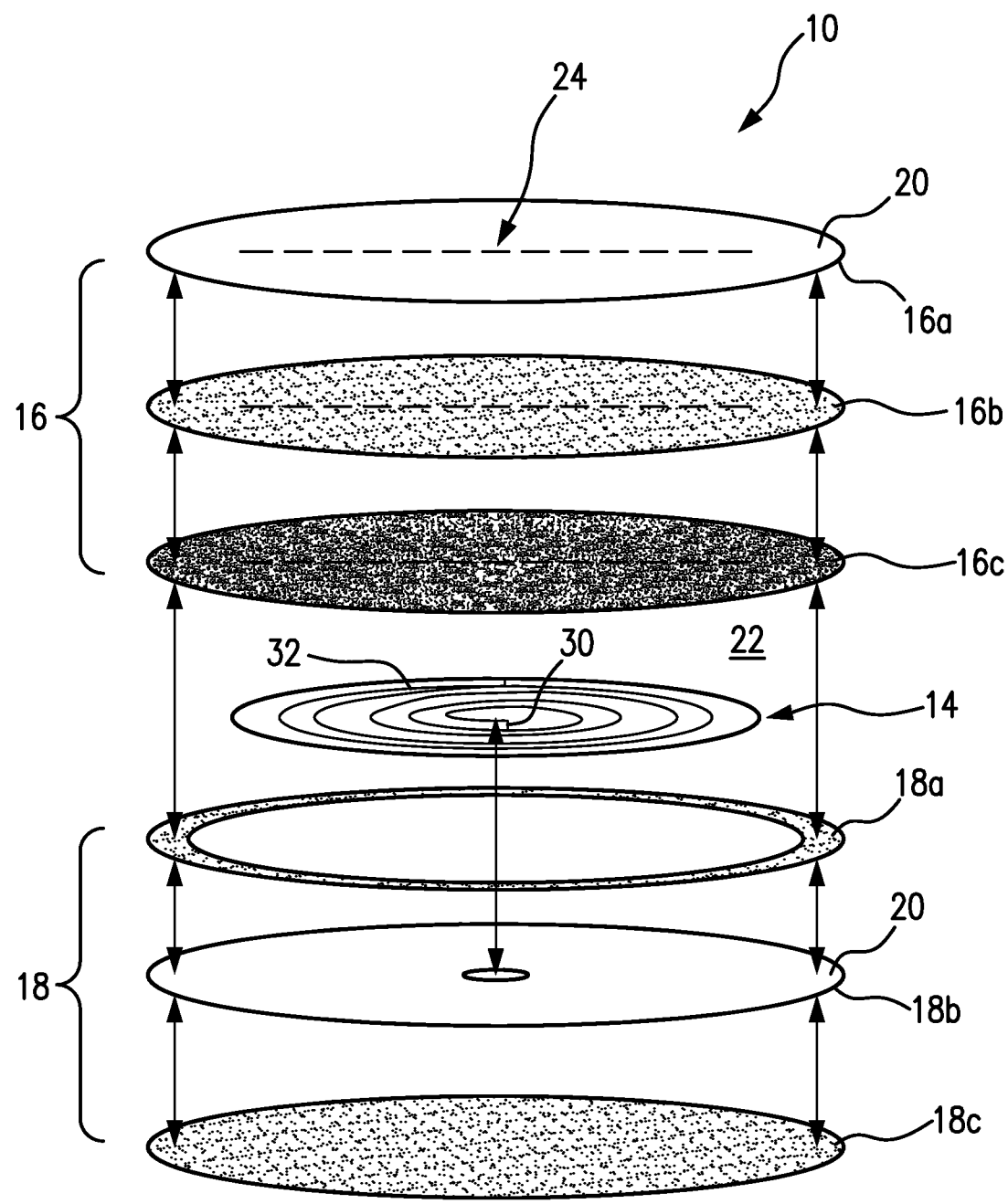
FIG. 1 is an exploded perspective view of a self-contained disposal-bag system according to a first example embodiment of the present invention, showing the major components of the system.
Figure 2:
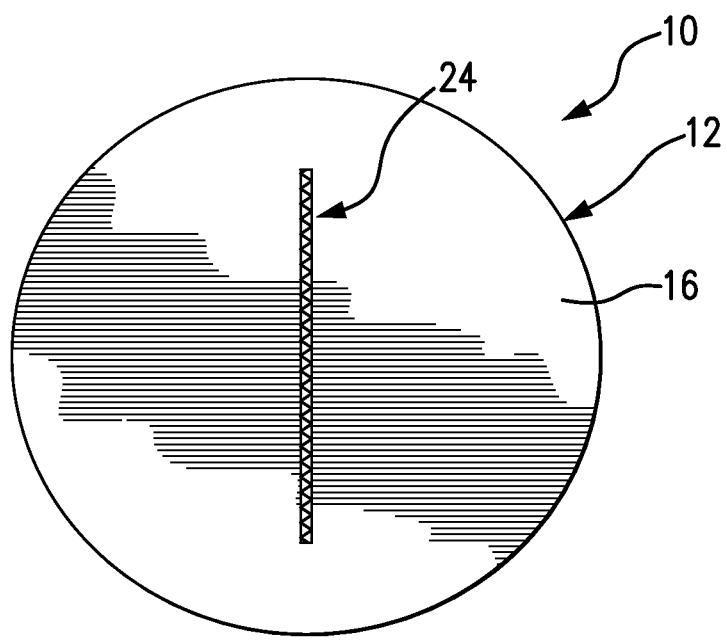
FIG. 2 is a plan view of the disposal-bag system of FIG. 1 in an assembled state.
Figure 3:
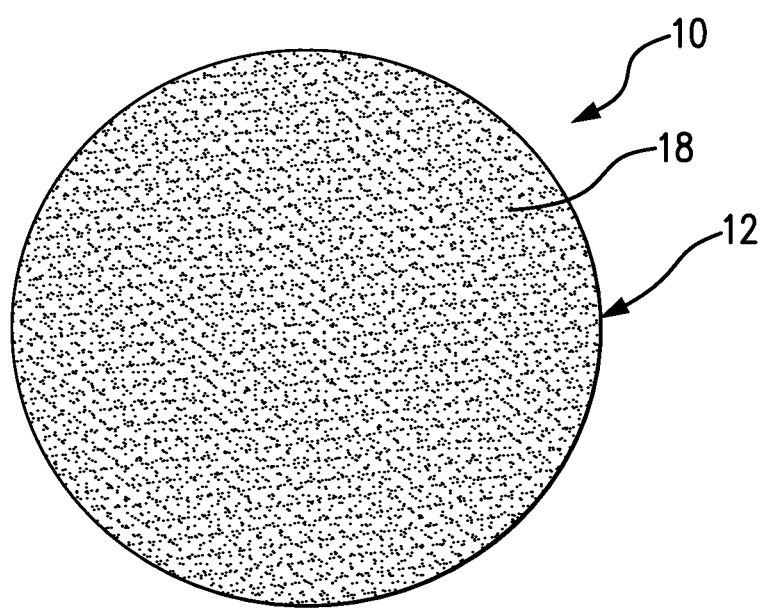
FIG. 3 is a bottom of the disposal-bag system of FIG. 2.
Figure 4:
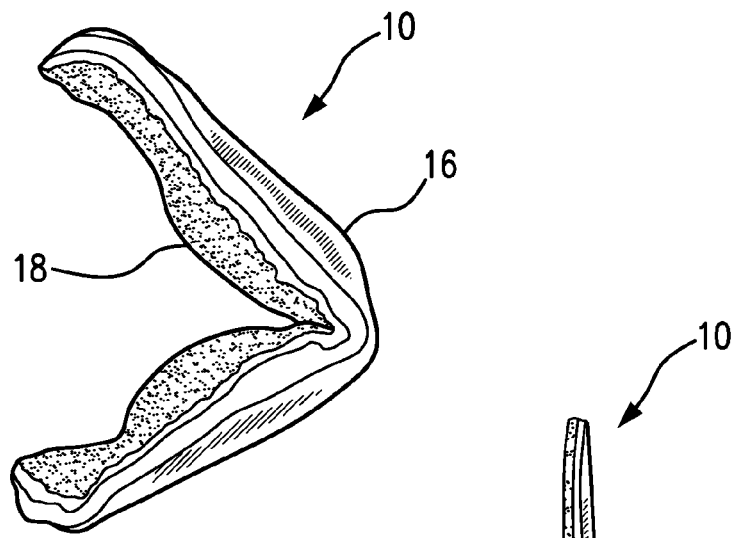
FIG. 4 is a side view of the disposal-bag system of FIG. 2 bent to show its flexibility.
Figure 5:
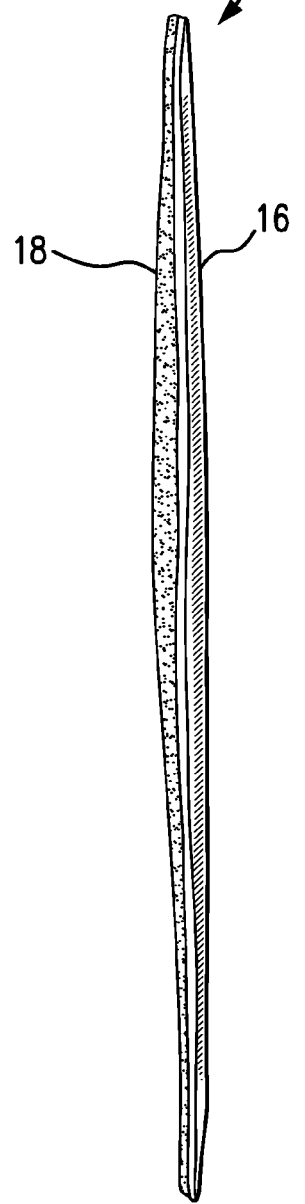
FIG. 5 is a side view of the disposal-bag system of FIG. 2 in its normal relaxed flat state.

The present invention relates to self-contained pod-like disposal-bag systems and methods for the disposal of disposable objects. In the embodiments described herein, the systems and methods are used for the disposal of disposable diapers, including standard commercially available disposable diapers or customized disposable diapers. It will be understood that while the depicted diapers are for infant use, the systems and methods can be easily adapted for use with adult diapers. In other embodiments, the systems and methods are adapted for use in the disposal of other disposable objects that are worn by humans (or other animals) for moisture absorption of bodily fluids, such as feminine hygiene products (e.g., sanitary pads, napkins, and liners) and medical-waste wound dressings, compression garments, and surgical-tray liners. And in still other embodiments, the systems and methods are used for the disposal of other disposable objects that contain bodily fluids, such as other medical waste (e.g., used sharps including scalpels, needles, and lancets, human tissue and body parts, and surgical equipment). It will be understood that, although the systems and methods detailed herein are illustrated with the disposable object being a diaper, the invention is not limited to diaper use and expressly includes systems and methods for the disposal of other disposable objects including those identified herein. It should be noted that the details described herein are representative and provided for illustration purposes only, and are not unnecessarily limiting of the invention.

FIGS. 1-31 show a self-contained disposal-bag system 10 according to a first example embodiment of the present invention. FIGS. 1-5 provide an overview of the system 10, FIGS. 6-14 show details of its construction, and FIGS. 15-31 show details of its use.

Referring to FIGS. 1-5, the disposal-bag system 10 includes a container 12 and a disposal bag 14 stored within the container. In the depicted embodiment, the container 12 has a top sheet 16 and a bottom sheet 18 (the "sheets 16/18") that are attached together around their peripheries 20 to form an internal cavity 22. In other embodiments, the container is formed of a single folded sheet, top and bottom sheets interconnected by one or more sidewalls, or other conventional low-profile containers. The top and bottom sheets 16/18 can be attached together by an adhesive, by stitching, or by other attachment elements known in the art. The bag 14 is folded into a generally flat, compact arrangement, held in the container cavity 22, and at least partially removable through an openable closure 24 in the container 12. The container closure 24 is designed so that it can be hand-manipulated from a closed state to an open state. Accordingly, the container 12, with the bag 14 inside, is generally thin and flat with a low profile so that the system 10 can be attached to a diaper 8 (see, e.g., FIG. 14) for later use when needed, without being obtrusive prior to that time during the normal wearing use of the diaper. In this way, the disposal-bag system provides a convenient, sanitary, and self-contained method of disposing of soiled diapers 8 or other disposable objects.

The container 12 is sized and shaped so that the cavity 22 is large enough to completely enclose the folded bag 14, but need not be any larger. And in embodiments in which the container 12 is sized and shaped so that the cavity 22 is larger than needed for holding only the folded bag 14, it is preferably only slightly larger. The bottom and top sheets 16/18 can be made of the same material, such as a soft flexible plastic and cotton composite woven material, or different materials, and they can each be made of a single layer or multiple layers. Using such materials, the container 12 is soft and flexible (see FIG. 4) so that it conforms to the shape of the diaper 8 and bends with the diaper during normal wearing use of the diaper.

In the typical commercial embodiment shown in FIGS. 1-5, the container 12 is generally disc-shaped (the sheets 16/18 are generally circular) with a thickness of about 0.50 cm (when in a relaxed/uncompressed state), a circumference of about 6.35 cm, a diameter of about 2.02 cm, and a weight of less than about 1.0 gram. The top sheet 16 of the container 12 includes a permeable top layer 16a of a cotton and plastic composite woven material (e.g., designed to match, decoratively and texture-wise, the outer surface of the back side of the diaper 8), a bottom layer 16c of a cotton material (e.g., strong and flexible Egyptian cotton), and an intermediate layer 16b of a conventional adhesive film (e.g., of the type commonly used in manufacturing diapers) for bonding the top and bottom layers together. And the bottom sheet 18 includes an intermediate layer 18b of a cotton material (e.g., strong and flexible Egyptian cotton), a bottom layer 18c of a conventional adhesive film (e.g., of the type commonly used in manufacturing diapers) for bonding the bottom layer to the diaper 8, and a top layer 18a of a conventional adhesive film (e.g., of the type commonly used in manufacturing diapers) for bonding the bottom layer to the diaper. The top layer 18a of the bottom sheet 18 can be a hot-melt adhesive film having an annular shape that bonds together only the peripheries 20 of the bottom-sheet intermediate layer 18b and the top-sheet bottom layer 16c using a conventional heat-stamping process, with the folded bag 14 positioned between them (and within the peripheries of the sheets) to seal the container 12 closed and form the cavity 22 with the bag in it. And the bottom layer 18c can be a hot-melt adhesive film that bonds the container 12 to the diaper 8 using a conventional heat-stamping process performed during or after the manufacture of the diaper so that the disposal-bag system 10 becomes a part of the diaper. Typically, the top-sheet layers 16a-c are bonded together first, then the bottom end of the bag 14 is bonded (e.g., by spot-heating or a hot-melt adhesive) to the bottom-sheet intermediate layer 18b, then the top and bottom sheets 16/18 are bonded together (using the bottom-sheet top layer 18a) with the bag 14 positioned between them, and then the assembled system 10 is bonded to the diaper 8. In other embodiments, the container can have a rectangular, polygonal, or other shape based on the bag-folding arrangement, and have a larger or smaller size based on the bag size and desired thickness.

The openable closure 24, through which the bag 14 can be accessed and extended (at least partially removed) from the container 12, is typically located in the top sheet 16. In some embodiments, however, the openable closure can be formed in a sidewall or other portion of the container. In the depicted embodiment, the openable closure 24 is provided by an elongated failure zone formed in the top sheet 16 so that, upon the application of opposite-directed forces to the top sheet on opposite sides of the zone when in the closed state, the top sheet is manipulated to the opened state by failing along the zone to form an elongated slit-like opening 26 (see, e.g., FIG. 17) in the top sheet. The failure zone can be provided by a score line, perforations, a smaller-thickness section, or in another way so that the zone fails as desired. In some embodiments, the openable closure 24 of the container 12 is of a child-resistant design. For example, in embodiments with the container openable closure 24 provided by a failure zone in the container top sheet 16, the failure zone can be formed so that adult ingenuity and hand/finger strength and dexterity is required for the failure zone to fail and thus be opened. This effectively renders the container closure 24 child-resistant, because children do not have the ingenuity or the strength and dexterity in their hands and fingers to open the closure 24 and access the bag 14 in the container 12. In alternative embodiments, the openable closure is provided by a pocket flap with hook-and-loop fasteners, snaps, buttons, or other conventional fasteners, a zipper, a drawstring, or by another conventional openable closure known by persons of ordinary skill in the art.

The disposal bag 14 can be provided by a conventional plastic disposal bag. In some embodiments, the bags 14 are scented and/or flexible/stretch bags. The bag 14 has a body 28 with a bottom end 30 and an open top end 32, and a conventional closure 34 for the open top end for sealing the bag top closed after a soiled diaper 8 has been placed in the bag body (see FIG. 6). In typical embodiments, the bag closure 34 is provided by tie-able loop handles, a drawstring, tie flaps, a ZIP-LOC slide-closure mechanism, or unattached twist ties, though others can be used. Preferably, the bag closure 34 is designed so that a relatively small opening remains in the bag top 32 when closed, so that the bag 14 is not completely sealed closed, to minimize the possibility of a diaper-filled bag exploding from compression. In the depicted embodiment, the bag 14 has a body 28 that is generally rectangular and about 8 inches long and about 6 inches wide, not including the top-end bag closure 34. And the bag closure 34 is provided by two rectangular loop handles that extend from opposite sides of the top end 32, are adapted for ease of tying together to close the bag 14, and are each about 8 inches long (see FIG. 28) or 4 inches long when laid flat and folded together (see FIG. 6). This size and shape bag 14 works well for diapers for infants up to about 18 months old, though bags with other sizes and shapes can be used with good results.

The disposal bag 14 is preferably attached to the container 12 so that when the bag is extended from the container the bag cannot be separated from the diaper 8 (without destroying the bag for its intended use). For example, the bottom end 30 of the bag, opposite from the open top end 32, can be heat-bonded with an adhesive to an inner surface of the container 12 such as the bottom-sheet intermediate layer 18b. In other embodiments, the bag 14 is attached at other portions (e.g., a lower portion of its side) and/or by other attachment elements (e.g., adhesive tape or plastic clips). In some embodiments, the bottom end 30 of the bag 14 is attached to the bottom sheet 18 at about the center of the bottom sheet, and in other embodiments the bottom end of the bag is attached to the bottom sheet along a radius line to position it for being spirally or helically coiled within the container 12. The bag 14 is folded into a flat, compact arrangement for storage in the container cavity 22 so that it can be easily pulled out of the container 12 for use (except for the bottom end 30 that is attached to and stays within the container). For example, each bag 14 can be folded over on itself several times lengthwise and/or folded into a spiral or helical configuration, with the open top end 32 positioned on top adjacent the container closure 24 so that it's visible/accessible when the container closure is opened (see FIGS. 6-16).

The disposal-bag system 10 can be engineered with multiple safeguards for the protection of children. For example, the bag-housing container 12 can be attached to the diaper 8 on the outer surface of the back side of the diaper, just above the buttock area (see FIG. 14). This placement of the disposal-bag system 10 on the diaper 8 helps inhibit access by a child wearing the diaper. In addition, the openable closure 24 of the container 12 can be of a child-resistant design so that children cannot open the closure and access the bag 14 in the container. Furthermore, the disposal-bag system 10 can be designed with the bag 14 tightly held in the container 12 (e.g., the container can be sized and shaped so that in a relaxed state the cavity 22 is the same size or slightly smaller than the folded bag) such that, once the container closure 24 is opened, it takes adult hand/finger dexterity and strength to pull out the bag for use (see FIG. 18-19). Moreover, the disposal-bag system 10 can be designed with the bag 14 attached to the container 12 so that, after the bag is extended from the container for use, it cannot be detached from the diaper 8 by the child wearing the diaper (see FIG. 11). Also, the disposal-bag system 10 can be designed with the bag 14 temporarily sealed in a folded arrangement by a pull tab 36 (which also functions as a safety adhesive release strip) and an impermanent bond edge 38 that helps keep the bag from unfolding and deploying in the hands of a child (see FIG. 10).

Having generally described the disposal-bag system 10 of this first example embodiment, details of its construction will now be described with respect to FIGS. 6-14. It will be understood that the method of making the disposal-bag system 10 described herein is provided for illustration purposes and is not limiting of the invention.

The method of making the disposal-bag system 10 can include the following steps, which can be performed using conventional mass-production manufacturing equipment and techniques as are known in the art. First, the bag 14 is laid flat as shown in FIG. 6, then folded in half lengthwise so that the loop-handle closures 32 are aligned together as shown in FIG. 7, then folded in half lengthwise a second time into quarter-sections as shown in FIG. 8. The loop-handle closures 32 are then folded down to between the folded body halves 28 (or this can be done after folding the bag 14 in half the first time), as shown in FIG. 9.

Figure 10:
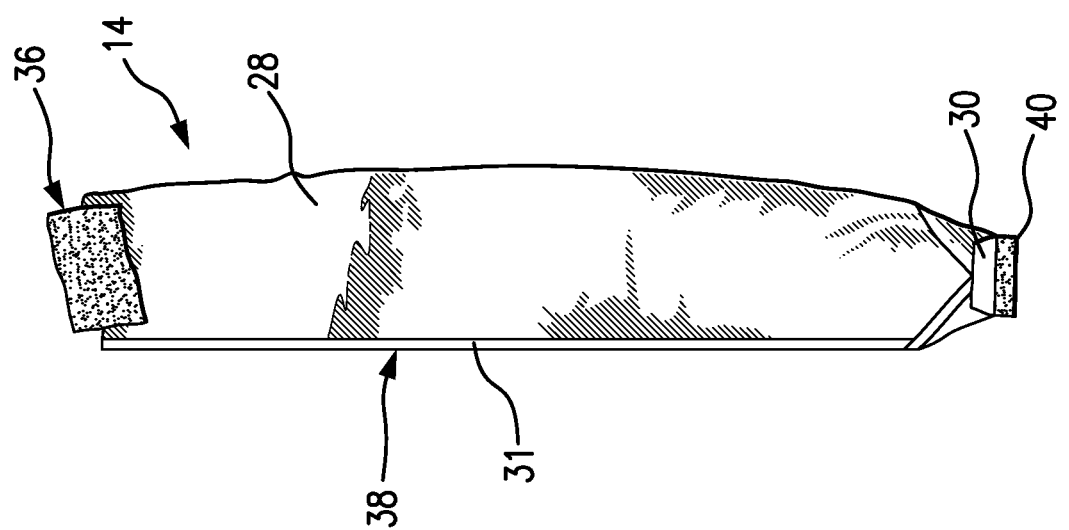
FIG. 10 shows the bag of FIG. 9 with its free side edges impermanently bonded together and a pull tab bonded to its top end adjacent the folded-in loop handles.

Then the top open end 32 of the body 28 of the bag 14 (which is to be positioned adjacent the container closure 24) can be safety sealed with the pull tab 36, as shown in FIG. 10. The pull tab 36 can be provided by a sheet of material (e.g., paper or plastic) with an adhesive backing and with marking (e.g., with the printed words "pull here") on its front/top side to inform the user to pull it. To install the pull tab 36, the adhesive backing is adhered to the bag 14 at the top end 32 on one side, then folded over and adhered to the opposite top end side. If desired, about one half of the adhesive backing can include an adhesive selected to be permanent under normal-use conditions so that the pull tab 36 will not easily pull completely off of the bag 14 and thus be separated from it without rendering the bag unusable for its intended purpose, thus not creating excess waste. In other embodiments, the pull tab is attached to the bag top by other attachment elements such as adhesive tape, plastic clips, or hook-and-loop fasteners, with or without safety sealing closed the bag top end 32, or it is omitted. In this way, the pull tab 36 functions as a convenient-to-use and easy-to-identify location (adjacent the container closure 24) for the user to pull to extend the bag 14 from the container 12 for use, while also functioning as a safety measure that minimizes the likelihood of an infant being able to open the bag and injure itself.

At this point, or before installing the pull tab 36, the aligned free side edges 31 of the folded bag 14 can be adhered together with the impermanent bond 38, as shown in FIG. 10. In typical embodiments, the impermanent bond 38 is formed by spot-heating an adhesive placed along the free side edges 31. In other embodiments, the impermanent bond is formed by other attachment elements such as adhesive tape, plastic clips, or hook-and-loop fasteners, it is formed along free edges of an unfolded or multi-folded bag, or it is omitted. The impermanent bond 38 is formed along the aligned free side edges 31 of the twice-folded bag (into quarter-sections) 14 to temporarily hold them together, with the bond having a strength such that the bag is retained in the twice-folded arrangement but an adult can slide a finger behind the bond into the space between the two halves of the twice-folded bag body 28 and slide the finger along the bond with a force sufficient to detach the bonded edges from each other so the bag can be unfolded for use (see also FIGS. 7-8 and 21). That is, adult ingenuity and hand/finger dexterity and strength is required to generate a force sufficient to overcome the bonding forces of the impermanent bond 38 to unfold the bag 14, so children are generally unable to open the bag.

Figure 11:
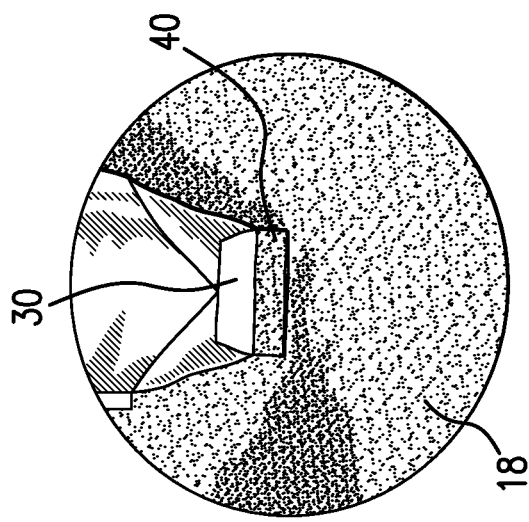
FIG. 11 shows the bag of FIG. 10 with its bottom folded diagonally and bonded to the bottom sheet of the disposal-bag container.

Next, the bottom end 30 of the bag 14 is attached to the container 12, as shown in FIG. 11. In typical embodiments, the bag bottom end 30 is attached to the container bottom sheet 18 by a permanent bond 40. The permanent bond 40 is formed by conventional techniques in order to keep the bag 14 securely attached to the container 12 when the adult user pulls the bag to extend it from the container during the normal and intended use. This functions as a safely feature to prevent the infant wearing the diaper from removing the bag 14 from the container 12 and injuring itself, and helps minimize separate waste pieces. For example, the permanent bond 40 can be formed by spot-heating an adhesive material. The bag bottom end 30 can be attached to the container bottom sheet 18 at about the center of the bottom sheet. If desired, the bag bottom end 30 can be funnel-folded (e.g., to about ½ inch wide), as depicted, by folding in each bottom corner at an angle and then folding up the bottom edge.

Figure 12:
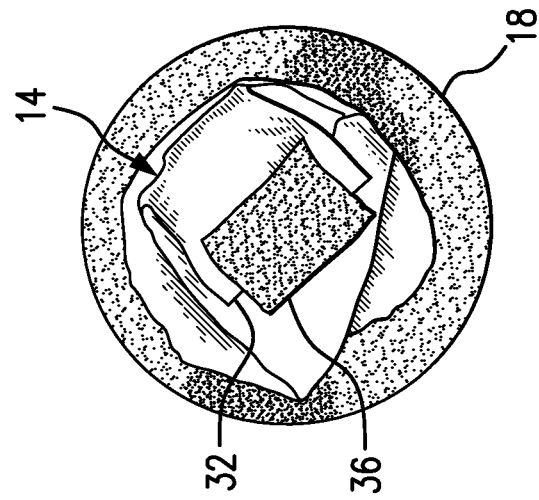
FIG. 12 shows the bag and bottom sheet of FIG. 11 with the bag folded flat into a spiral configuration.

Next, the bag 14 is folded into a flat compact arrangement and laid flat against the bottom sheet 18 with the pull tab 36 on top so that it will be positioned adjacent the container closure 24 after assembly, as shown in FIG. 12. In typical embodiments, the bag 14 is folded into a spiral or helical configuration (e.g., about 5.08 cm in circumference). Then the top sheet 16 is attached to the bottom sheet 18 to complete the assembly, with the folded bag 14 positioned between them to form the cavity 22. In typical embodiments, the sheets 16/18 are attached together by a hot-melt adhesive, though alternatively they can be stitched together or attached using other conventional attachment elements such as mating screw-threading or snap-fit detents.

Figure 13:
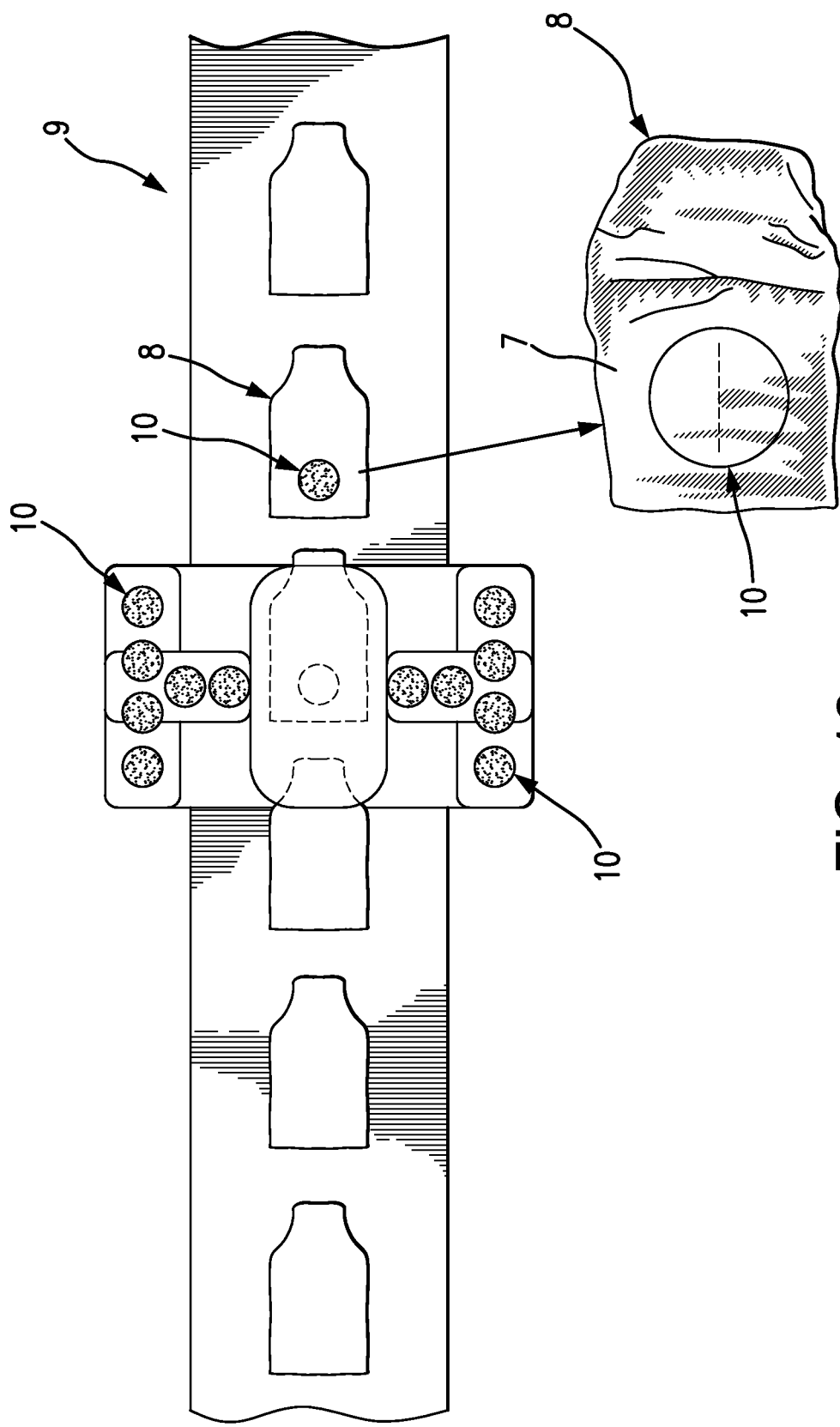
FIG. 13 shows the disposal-bag system of FIG. 12, with the top sheet assembled onto the bag and bottom sheet to complete the assembly, and with the assembled disposal-bag system being applied to a diaper.

The disposal-bag system 10 can be attached to a disposable diaper 8 as shown in FIG. 13. The diapers 8 can be manufactured using conventional diaper-manufacturing equipment and techniques on an assembly line. Typically, this involves forming an absorbent inner layer (the diaper core), merging and gluing layers of plastic film and fabric together to form a backing, then gluing the core to the backing. The disposal-bag systems 10 can be attached to the diapers 8 as an additional step in the manufacturing process of the diapers on the diaper assembly line. For example, the disposal-bag systems 10 can be heat-stamped onto the diaper backing 7 just prior to applying the elastic around the diaper waist and leg openings and the diaper-cutting and -folding process. So after the disposal-bag system 10 is attached to the diaper backing 7, the diaper core and backing (now with a disposal-bag system attached) are then merged together, cut, folded, and packaged to complete the manufacture of the diaper 8. Thus, the attachment of the disposal-bag systems 10 to the diapers 8 can be done as an additional step in the diaper-manufacturing process. For example, the depicted diaper-manufacturing equipment 9 includes a conveyor belt carrying a plurality of the diapers 8, a hopper holding a plurality of the disposal-bag systems 10 and feeding them into position for attachment to the diapers, and a heat-stamping mechanism for bonding the disposal-bag systems to the diapers. Persons of ordinary skill in the art will appreciate that the disposal-bag systems 10 can be attached to disposable diapers 8 using other equipment and techniques that are known in the art.

Figure 14:
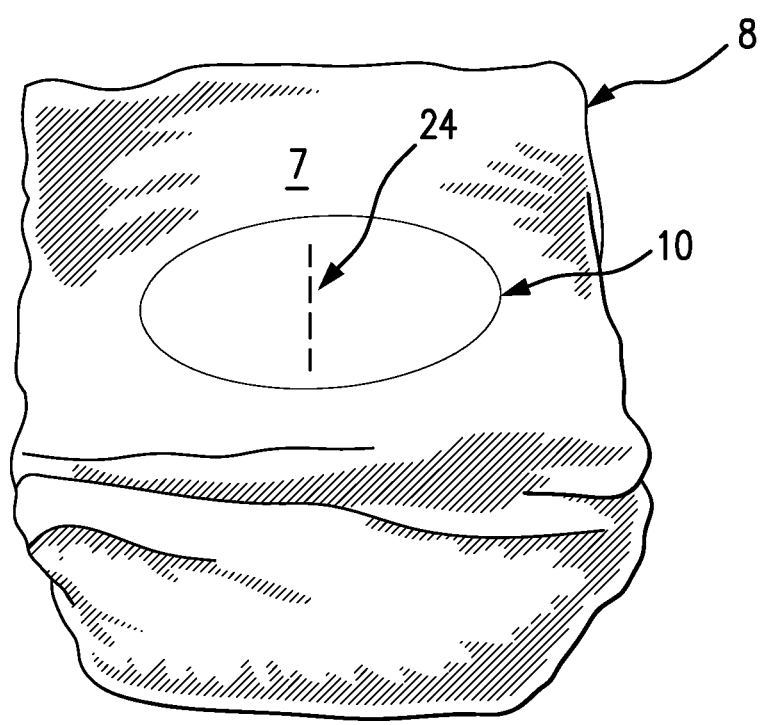
FIG. 14 shows the diaper and the disposal-bag system of FIG. 13 assembled together and ready for use.

FIG. 14 shows the completed assembly of one of the diapers 8 with one of the disposal-bag systems 10 attached to it. In the depicted embodiment, the disposal-bag system 10 is attached to the backing 7 of the diaper 8 just above the buttock area of the diaper. In this position, the disposal-bag system 10 is unobtrusively located, and it's most difficult for the infant wearing the diaper 8 to reach the disposal-bag system and try opening it and accessing the bag 14. In other embodiments, the disposal-bag systems 10 can be applied to the diapers 8 in other locations.

Having described an example method of manufacturing the disposal-bag system 10 of this first example embodiment, details of its method of use will now be described with respect to FIGS. 15-31. It will be understood that the herein-described method of using the disposal-bag system 10 to dispose of a soiled diaper 8 is provided for illustration purposes and is not limiting of the invention. The method includes providing a diaper 8 with a self-contained disposal-bag system 10 attached to it. The disposal-bag system can be provided by any of the disposal-bag systems described herein or variations or derivatives of them.

The method of use includes the steps of removing a soiled diaper 8 from a child, laying the diaper flat with the disposal-bag system 10 facing down, rolling up the soiled diaper starting from the bottom, and bringing together the diaper's two stretch side panels to secure the rolled diaper into a bundle as shown in FIG. 15, with the disposal-bag system still exposed and accessible. Then the rolled-up diaper 8 is flipped over to present the disposal-bag system 10 on the back side 7 of the diaper, and the container closure 24 is manipulated form its closed state to its opened state. This can be done, for example, by an adult user placing his thumbs on both sides of a failure-zone-type container closure 24 and applying laterally outward pressure until the closure fails, which thereby forms the opening 26 in the container top sheet 16, as shown in FIGS. 16-17. Then the bag 14 is extended from the container 12 for use. This can be done, for example, by reaching the thumb and index finger into the opening 26 and grasping the pull tab 36 attached to the bag 14 (or grasping the bag itself) and pulling the bag outward through the opening, as shown in FIG. 18. The bag 14 is pulled until it is extended from the container 12 to its maximum length, with its bottom end 30 still attached to and within the container, as shown in FIG. 19.

Figure 22:
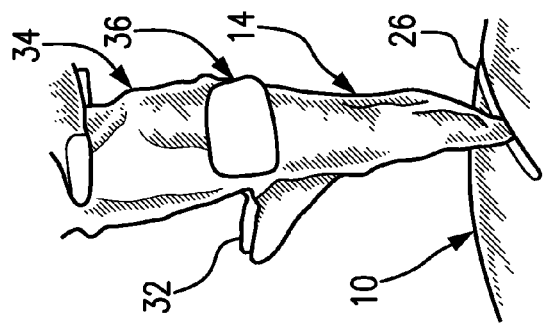
FIG. 22 shows the rolled-up diaper and disposal-bag system of FIG. 21 with the loop handles of the bag being unfolded.
Figure 21:
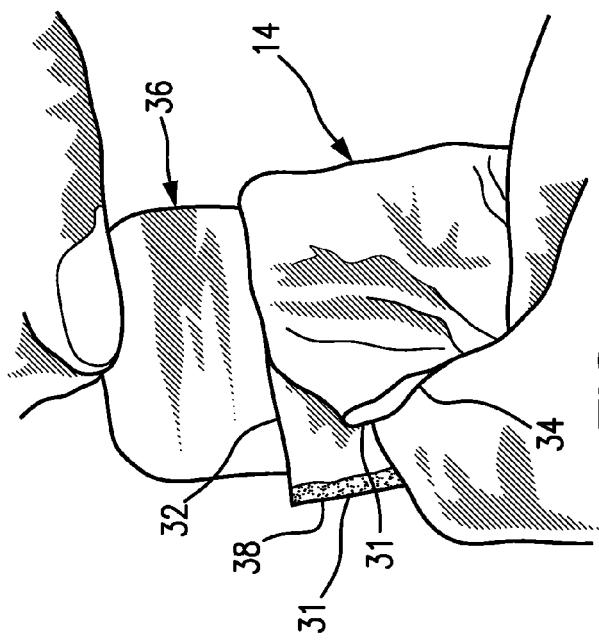
FIG. 21 shows the rolled-up diaper and disposal-bag system of FIG. 20 with a user's index finger sliding vertically to break the impermanent bond of the side edges of the bag.
Figure 23:
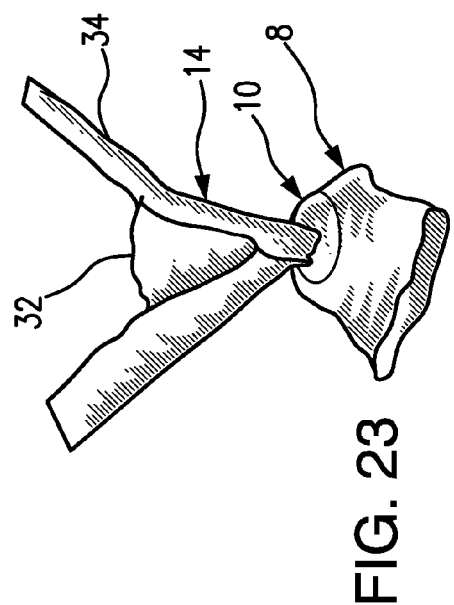
FIG. 23 shows the rolled-up diaper and disposal-bag system of FIG. 22 with the loop handles of the bag being separated from each other.
Figure 20:
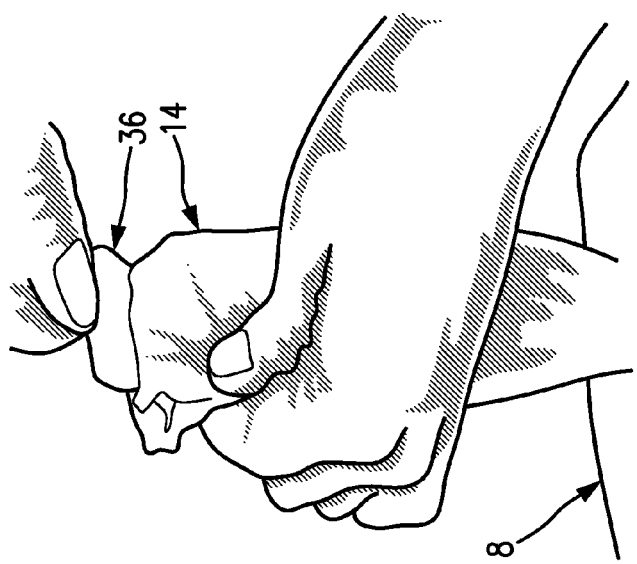
FIG. 20 shows the rolled-up diaper and disposal-bag system of FIG. 19 with the pull tab being removed from the top of the bag.

Then at least one end of the pull tab 36 is removed from the bag 14 and the impermanent bond 38 of the free sides edges 31 of the bag is released, as shown in FIGS. 20-21. For example, about one half-portion of the pull tab 36 can be peeled back (e.g., a label can be provided instructing the user which half-portion to remove), leaving the other about half-portion still permanently attached to the bag 14, as depicted, so that the folded-in loop handles can be unfolded. And the adult user can insert an index finger between the folded-bag quarter-sections (e.g., at the bag top 32 where the pull tab 36 was) and slide the finger down to break the impermanent bond 38, as depicted, and thereby detach/release the bonded side edges 31 from each other so the bag 14 can be unfolded. Then the loop-handle closures 34 of the bag 14 are unfolded, as shown in FIG. 22, and separated from each other, as shown in FIG. 23, to fully open the bag, as shown in FIG. 24.

Figure 31:
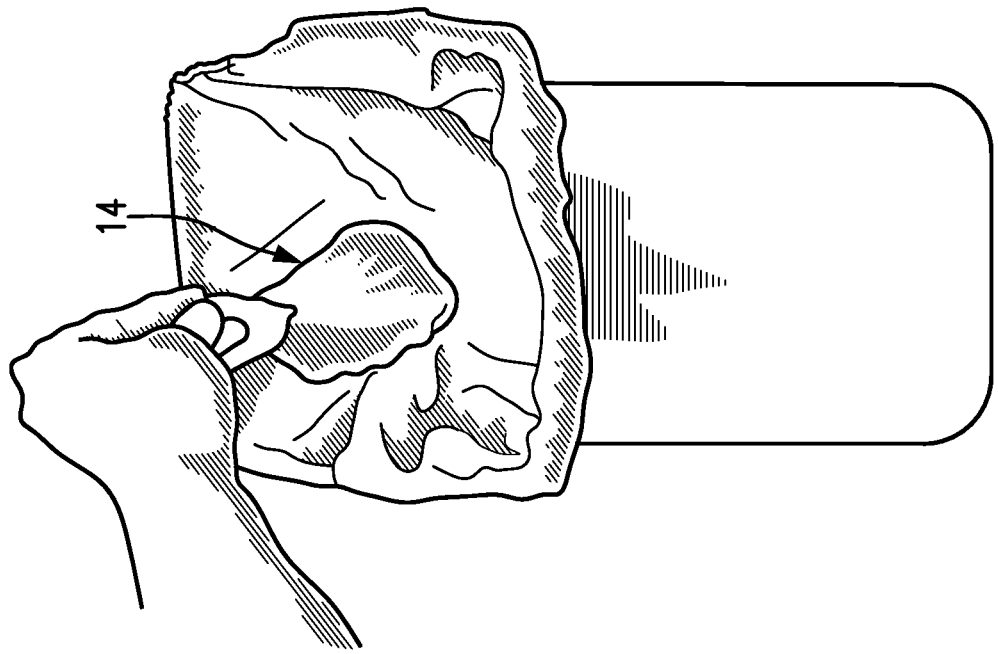
FIG. 31 shows the rolled-up diaper and disposal-bag system of FIG. 30 with the closed diaper-containing bag being deposited in a trash receptacle.
Figure 30:
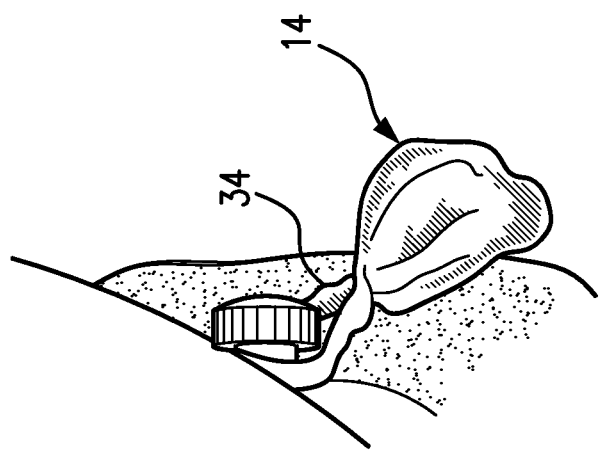
FIG. 30 shows the rolled-up diaper and disposal-bag system of FIG. 29 with the closed diaper-containing bag hung from a baby stroller for temporary storage.
Figure 32:
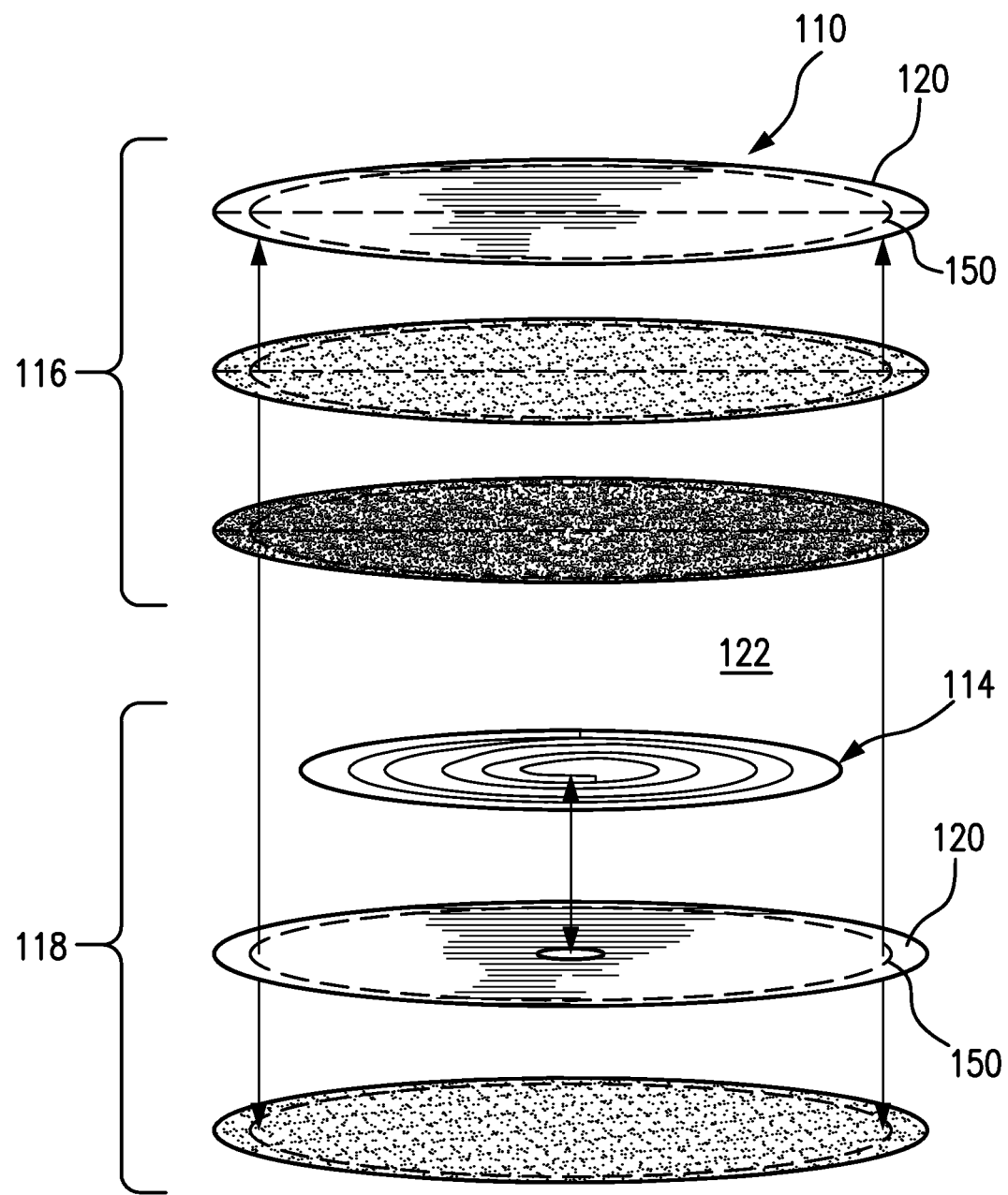
FIG. 32 is an exploded perspective view of a self-contained disposal-bag system according to a second example embodiment of the present invention, showing the major components of the system.
Figure 33:
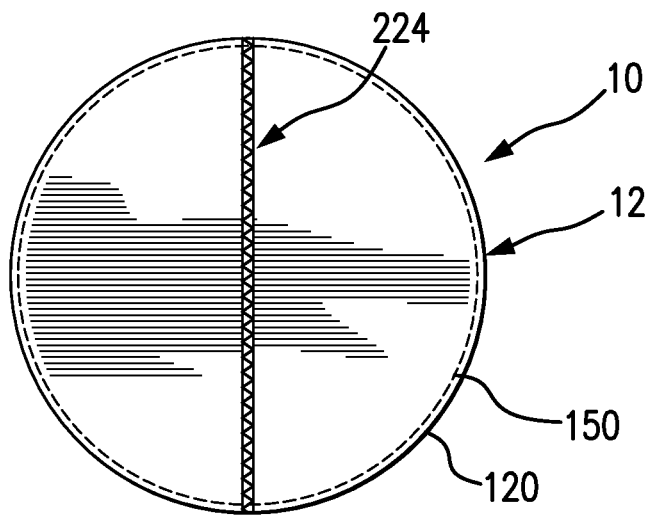
FIG. 33 is a plan view of the disposal-bag system of FIG. 32 in an assembled state.
Figure 34:
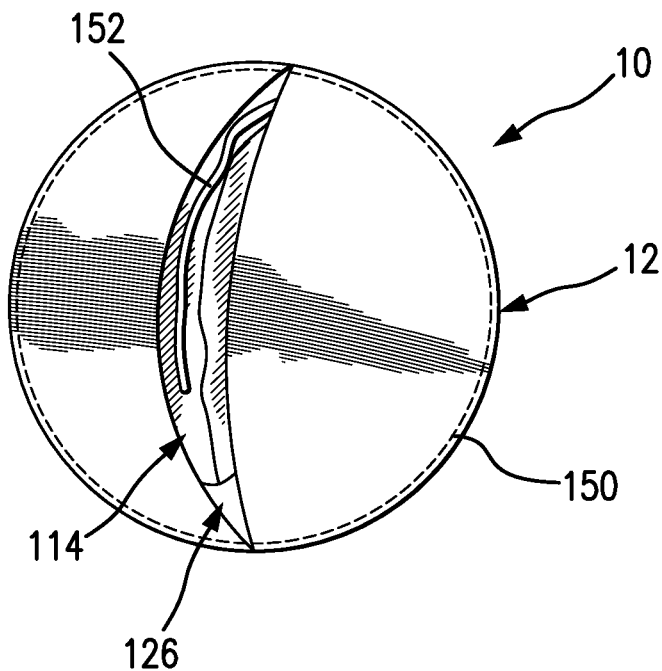
FIG. 34 shows the disposal-bag system of FIG. 32 in a partially opened state.
Figure 38:
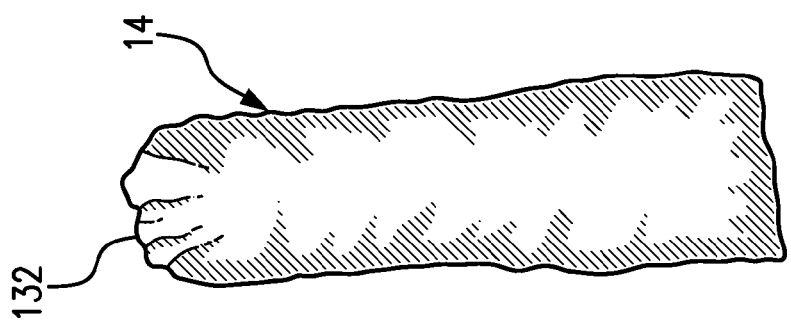
Figure 37:
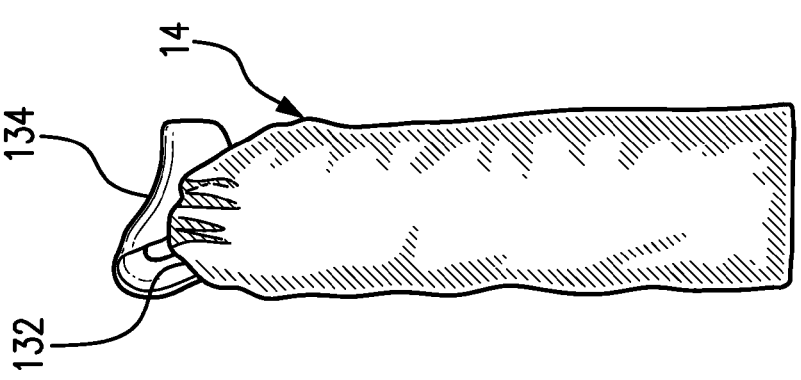
FIG. 37 shows the bag of FIG. 36 folded over again (twice total).
Figure 36:
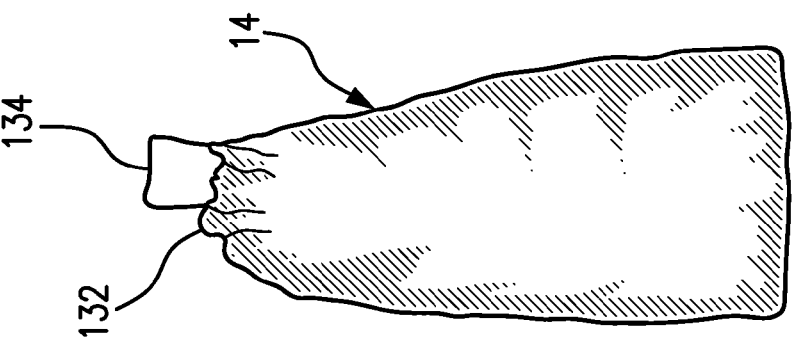
FIG. 36 shows the bag of FIG. 35 folded over once.
Figure 35:
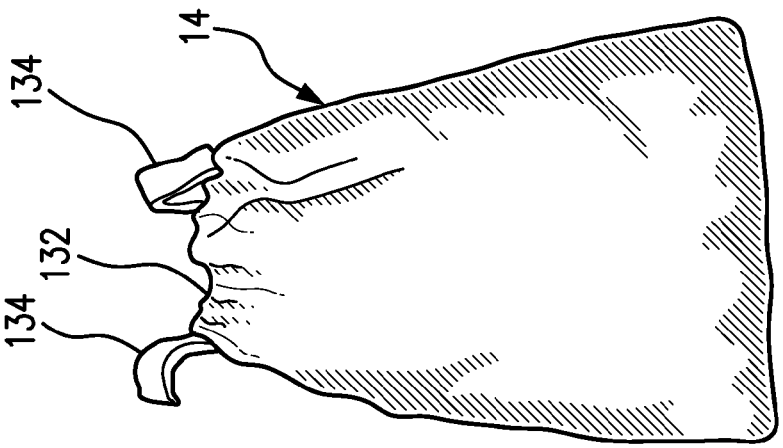
FIG. 35 is a plan view of the disposal bag of the disposal-bag system of FIG. 33, showing the disposal bag laid flat according to a second example method of manufacturing the disposal-bag system.
Figure 41:
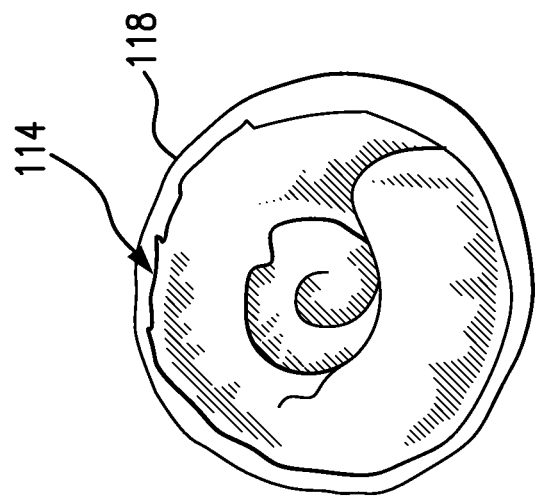
FIG. 41 shows the bag and bottom sheet of FIG. 40 with the bag folded flat into a spiral configuration.
Figure 40:
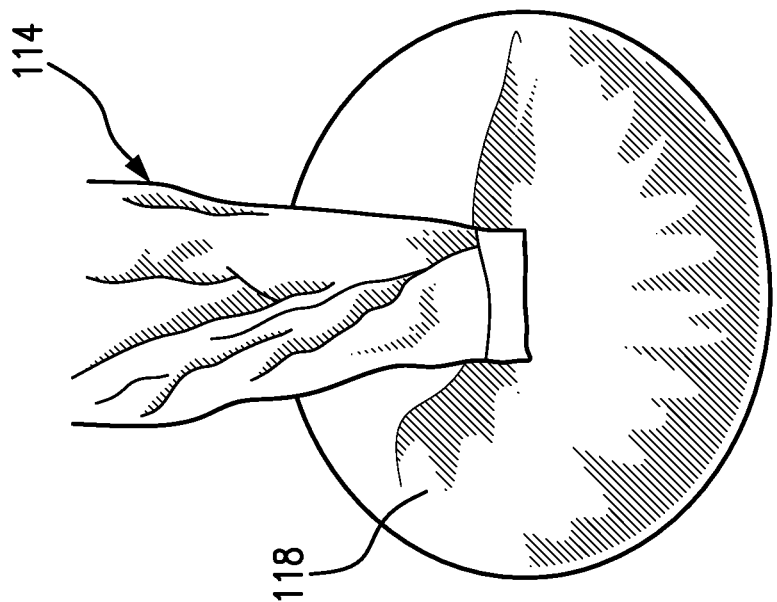
FIG. 40 shows the bag of FIG. 39 with its bottom bonded to the bottom sheet of the disposal-bag container.
Figure 39:
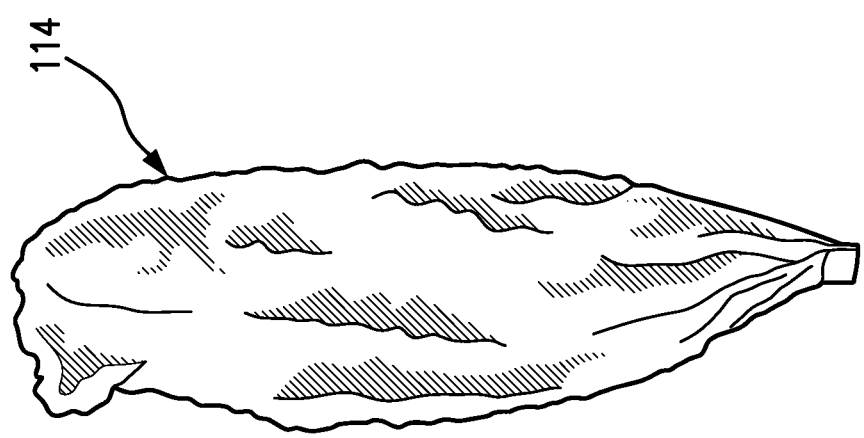
FIG. 39 shows the bag of FIG. 38 with its bottom diagonally funnel-folded.
Figure 46:
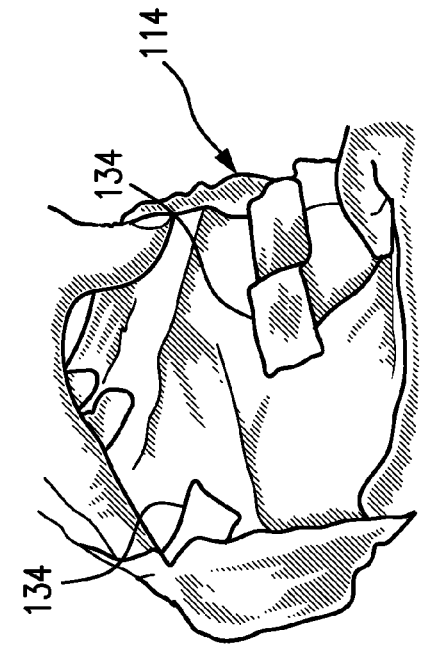
FIG. 46 shows the rolled-up diaper and disposal-bag system of FIG. 45 with the bag fully opened and its drawstring exposed portions being unfolded.
Figure 45:
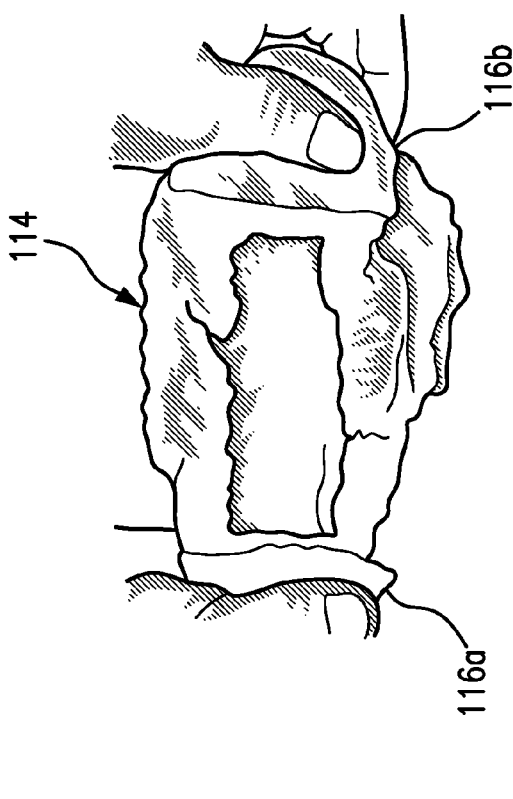
FIG. 45 shows the rolled-up diaper and disposal-bag system of FIG. 44 with the two top sheet sections being pulled apart to open the bag.
Figure 49:
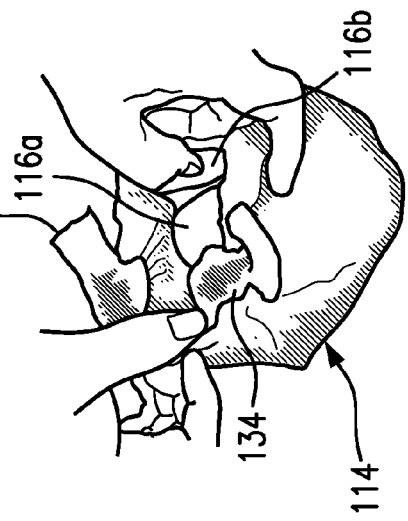
FIG. 49 shows the rolled-up diaper and disposal-bag system of FIG. 48 with the bag with its top sheet sections being folded into the inverted bag.
Figure 48:
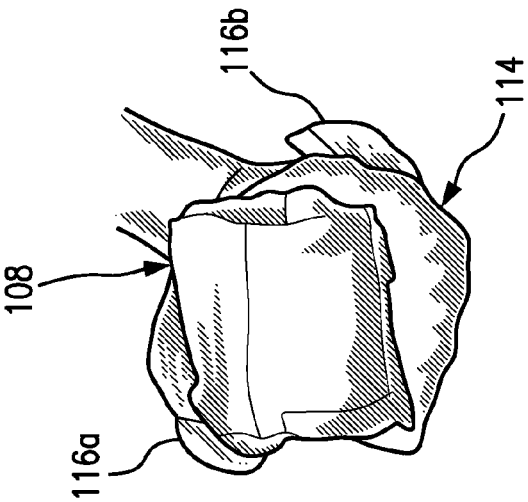
FIG. 48 shows the rolled-up diaper and disposal-bag system of FIG. 47 with the bag being inverted inside-out.
Figure 47:
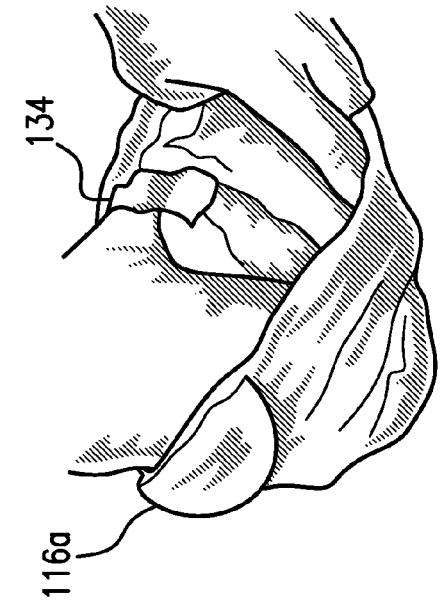
FIG. 47 shows the rolled-up diaper and disposal-bag system of FIG. 46 with the user's hand reaching into the bag to grasp the diaper.
Figure 50:
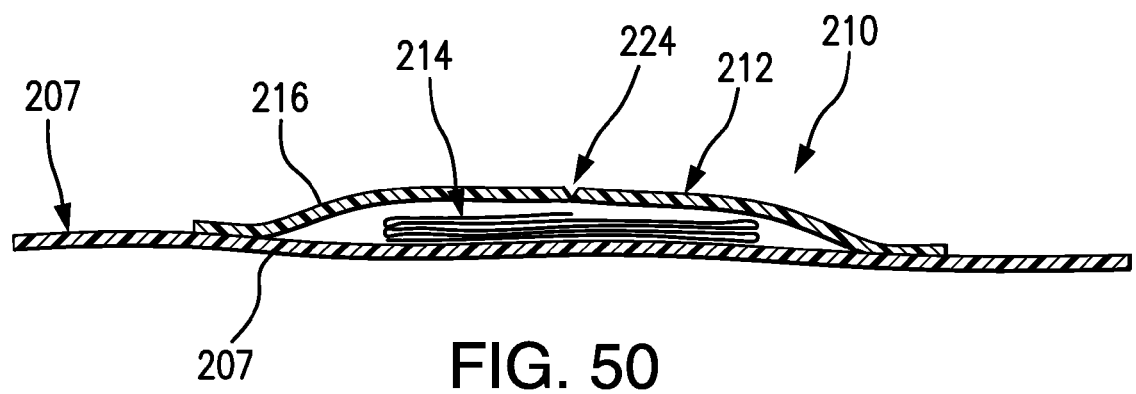
FIG. 50 is a cross-sectional view of a self-contained disposal-bag system according to a third example embodiment of the present invention, with the bottom sheet of the container defined by the outer sheet of the diaper.
Figure 51:
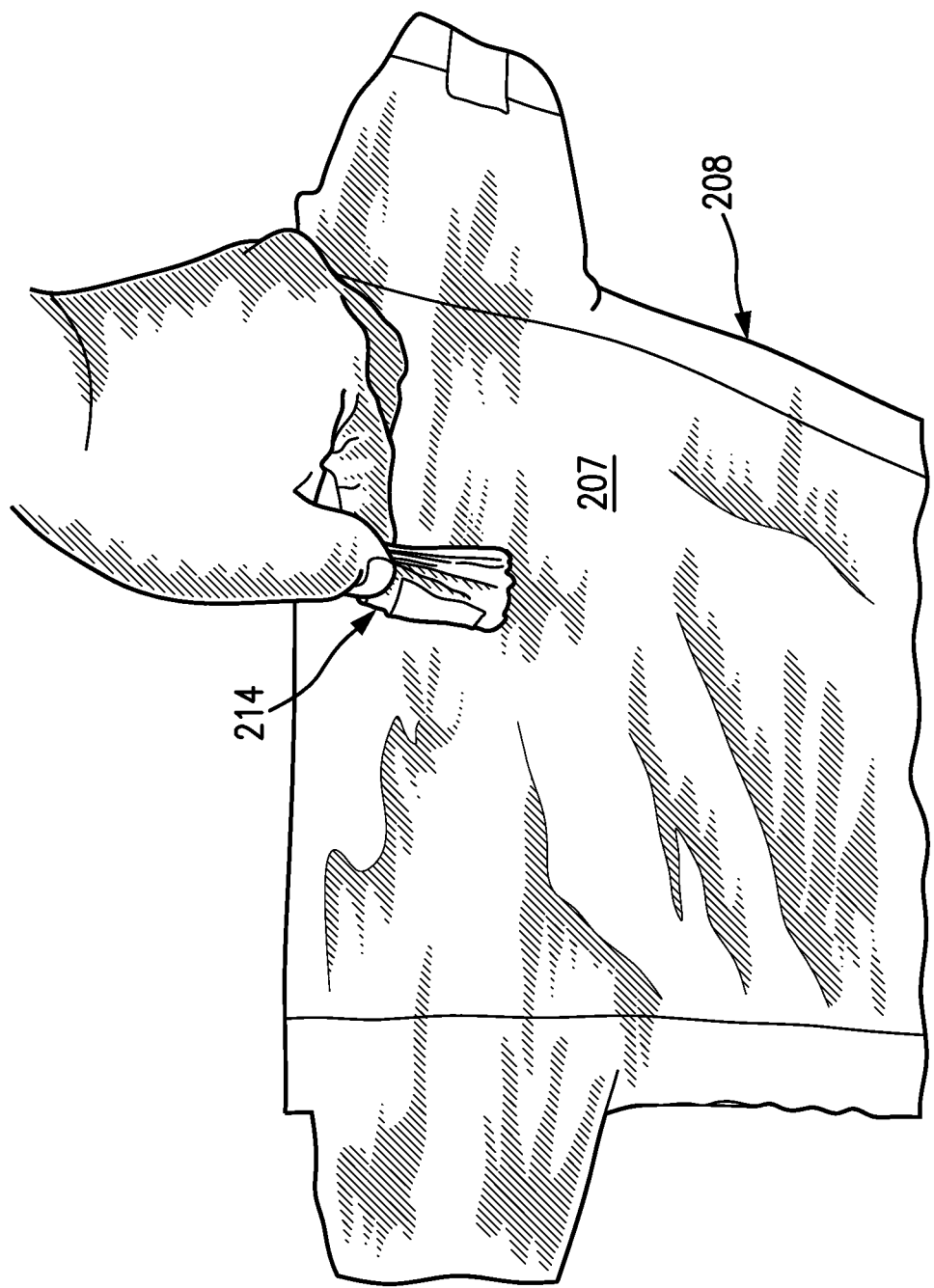
FIG. 51 is a plan view of the disposal-bag system and diaper of FIG. 50 during assembly, with a disposal bag folded flat into a compact arrangement.
Figure 52:
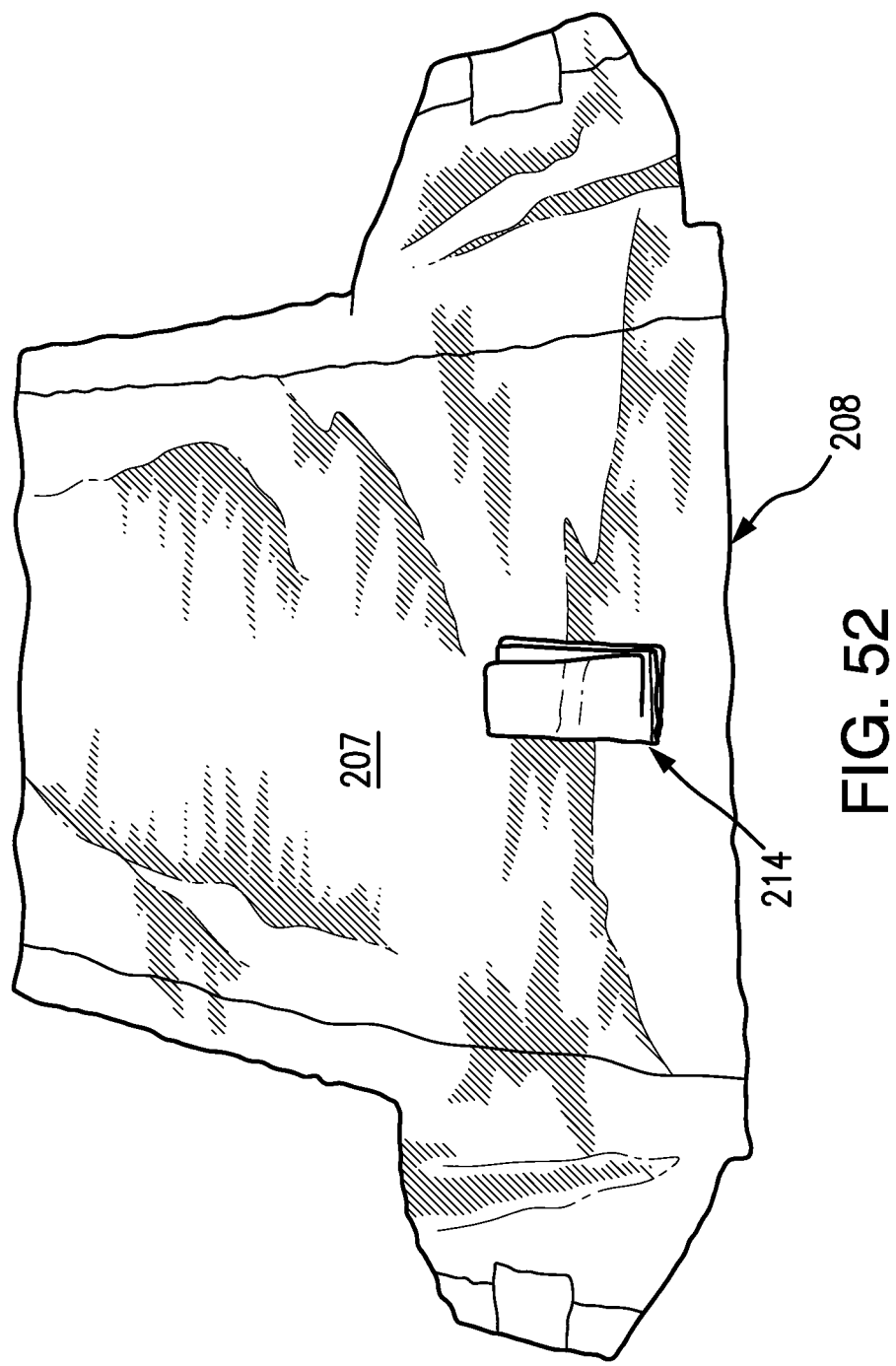
FIG. 52 shows the bag of FIG. 51 attached to the outer sheet of the diaper.
Figure 53:
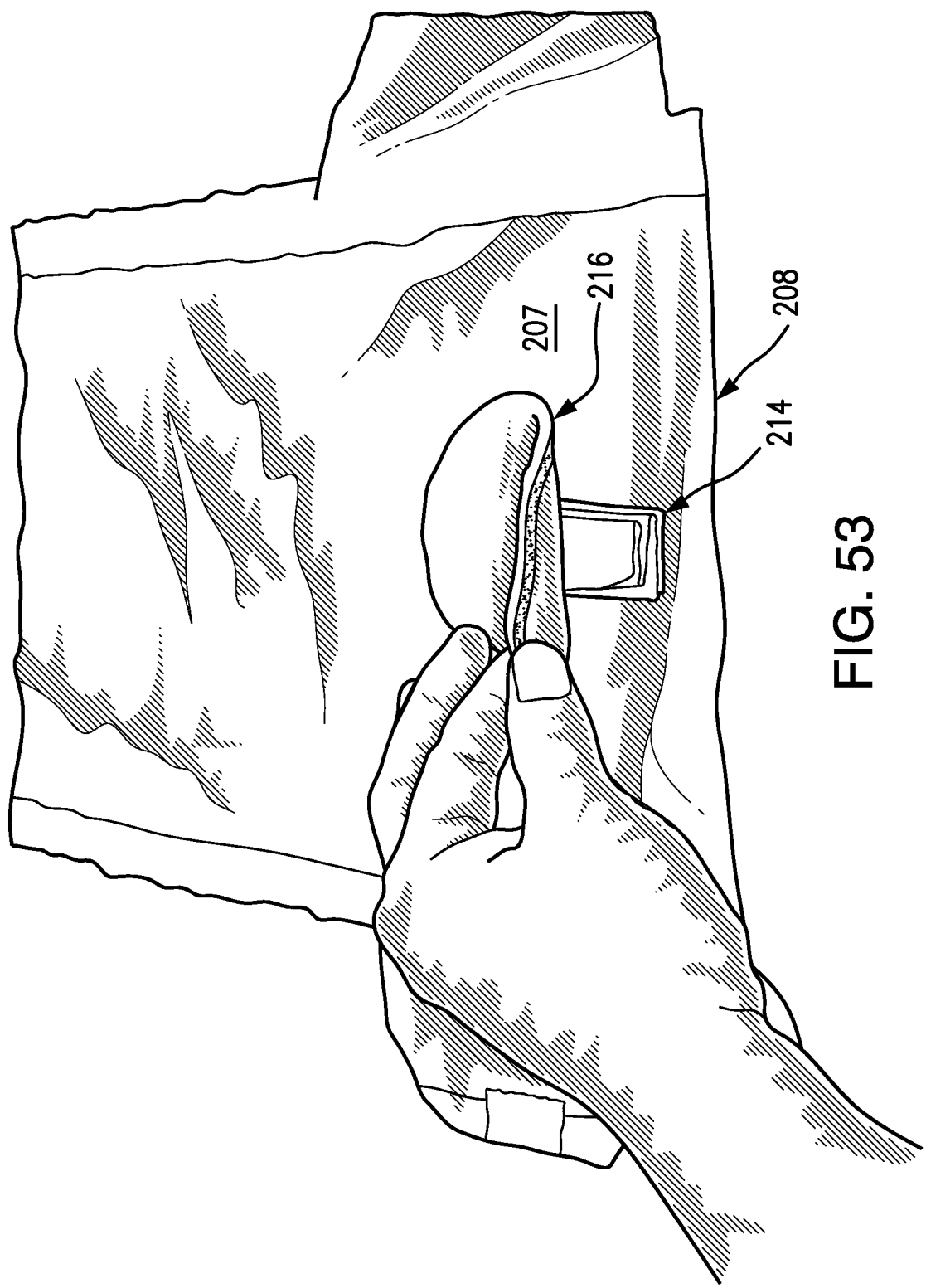
FIG. 53 shows the top sheet being attached to the outer sheet of the diaper of FIG. 52 to form the container for the bag.
Figure 54:
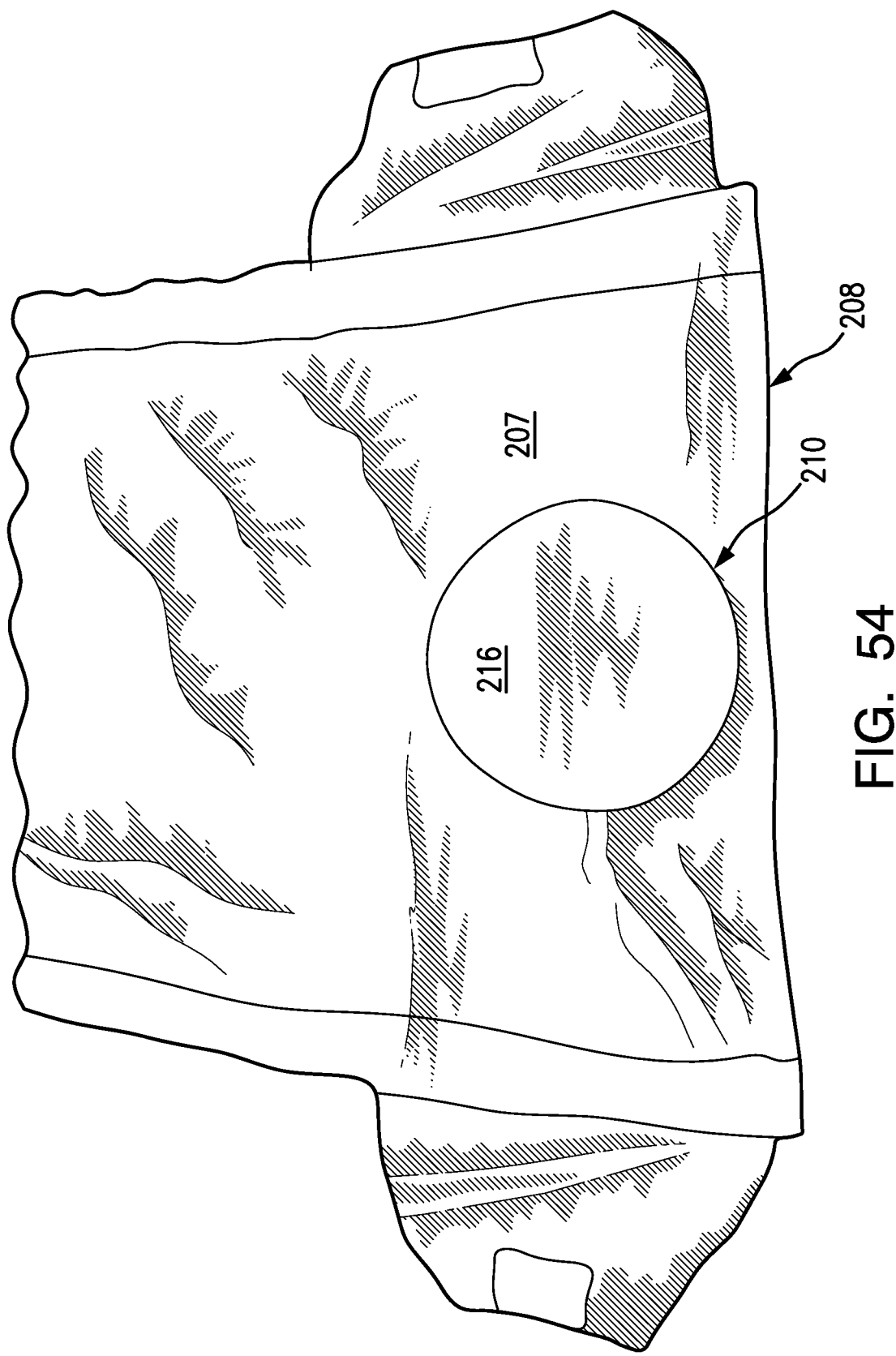
FIG. 54 shows the assembled disposal-bag system and diaper of FIG. 50.

Next, the user reaches one hand into the bag 14 and the grasps the rolled-up diaper 8, effectively using the bag as a glove, as shown in FIG. 25. Then the user inverts the bag 14 so that it is turned inside-out, so that the bag is pulled over the rolled-up diaper until the diaper is now within the inverted bag, as shown in FIGS. 26-27. Finally, the bag 14 is closed by the bag closure 34 to prevent the escape of offensive odor-causing bacteria and germs emanating from the diaper 8. For example, the loop-handle closures 34 can be tied together into a knot, as shown in FIGS. 28-29. The diaper-containing bag 14 can be stored temporarily for later disposal, for example by hanging it from a baby stroller as shown in FIG. 30, or it can be immediately deposited in a trash receptacle, as shown in FIG. 31. In this way, the use of the disposal-bag system 10 contributes to a more odor-free and sanitary disposal of the soiled diaper.

Having described the structure, manufacture, and use of the disposal-bag system 10 of the first example embodiment, additional example embodiments will now be described to better illustrate the full scope of the invention. It will be understood that any of the features of any of the herein-described embodiments can be combined to form an additional embodiment.

FIGS. 32-49 show a self-contained disposal-bag system 110 according to a second example embodiment of the invention. While the disposal-bag system 10 of the first example embodiment is well-suited for (but not limited to) use with diapers for infants up to about 18 months old, the disposal-bag system 110 of the second example embodiment is well-suited for (but not limited to) use with diapers for toddlers aged about 18 months and older. The disposal-bag system 110 is similar to the disposal-bag system 10 of the first example embodiment in that it includes a container 112 and a bag 114 stored in the container. And the container 112 can be similarly constructed with multi-layer top and bottom sheets 116 and 118 that are made of similar materials and have similar dimensions. Thus, the basic structure, manufacture, and use of the disposal-bag system 110 are similar, with a few notable exceptions.

The bag 114 of this embodiment can be larger and/or made of a stretchable plastic material for holding a larger diaper (plus a few wipes). In typical embodiments, the bag 114 is about 6 inches wide and about 5 inches long in a relaxed state, and can be stretched easily to 10 inches long. In addition, the bag 114 has a drawstring closure 134 at its top open end 132. Accordingly, the method of making the disposal-bag system 110 is modified to substitute in folding in the two exposed handle portions (e.g., which can be about 4 inches long) of the drawstring closure 134 in the process of folding the bag 114 over on itself twice, attaching it to the bottom sheet, and spiral-folding it flat, as shown in FIGS. 35-41.

In addition, the top and bottom sheets 116/118 of the container 112 are attached together by a releasable attachment assembly. In typical commercial embodiments, the releasable attachment assembly includes pull-away stitching 150 interconnected to an exposed pull-string 152. The pull-away stitching 150 attaches together the peripheral edges 120 of the top and bottom sheets 116/118. When the pull-string 152 is pulled, the stitching 152 is pulled out and thereby releases the top sheet 116 from the bottom sheet 118. In this embodiment, the container closure 124 is provided by a failure zone extending the entire diameter of the top sheet 116 such that upon applying a sufficient force the failure zone in the top sheet fails and the top sheet separates into two pieces 116a and 116b (e.g., halves). And the top sheet pieces 116a and 116b are attached to the bag 114 (e.g., by an adhesive) so that they can be pulled to extend the bag from the container 112. Accordingly the method of using the disposal-bag system 110 (applied to a diaper 108) is modified to substitute in reaching into the opening 126 formed when the container closure 124 is opened, pulling the pull-string 152 around the periphery 120 of the container 112 to separate the top and bottom sheets 116/118 from each other and to separate the top sheets into its two pieces 116a and 116b while leaving the bottom sheet 118 still attached to the diaper and the top sheet pieces still attached to the bag (see FIGS. 42-44), pulling the two top-sheet pieces together to extend the bag 114 from the container, pulling the two top-sheet pieces apart to open the bag (see FIG. 45), reaching into the bag to grasp the diaper (see FIGS. 46-48), inverting the bag inside-out until the diaper is within the bag, flipping the two still-attached top-sheet pieces into the inverted bag (see FIG. 49), and closing the bag with the drawstring closure 134.

In alternative embodiments, the releasable attachment assembly includes an exposed pull-string portion extending from a non-exposed pull-string portion positioned beneath a peripheral failure zone in the top sheet and in a peripheral seal zone attaching the top and bottom sheets together, with the failure-zone closure extending at least the entire diameter of the peripheral seal zone. And in other embodiments, the releasable attachment assembly includes other types of conventional releasable attachment assemblies that releasably hold the top and bottom sheets together, such as hook-and-loop fasteners, snap-fit detents, zippers, buttons, ZIP-LOC slide-closure mechanisms, or plastic clips.

Furthermore, the drawstring closure 134 of the bag 114 of the disposal-bag system 110 can include an elastic band wrapped around the lip of the bag's open top end 132, with the two exposed portions of the drawstring attached to the elastic band on opposite sides of the bag open top. In the method of use, with the top sheet 116 removed, the elastic band is stretched longer by pulling apart the two top sheet pieces 116a and 116b that are still attached to the open end 130 of the bag 114.

In another embodiment, the disposal-bag system includes a scent module that is activated upon opening the container. The scent module functions to release a scent/aroma when the container closure is opened, thereby helping to mask the smell of the soiled diaper.

FIGS. 50-54 show a self-contained disposal-bag system 210 according to a third example embodiment of the present invention. This embodiment is similar to those described above, in that it includes a container 212 and a disposal bag 214 stored within the container and extendible from the container through an openable closure 224. In this embodiment, however, the bottom sheet of the container 212 is defined by the backing 207 (the outer sheet) of the diaper 208. To make the system 210, the bag 214 can be attached to diaper backing 207 (which in this case is also the container bottom sheet) and then the top sheet 216 attached to the backing.

Figure 55:
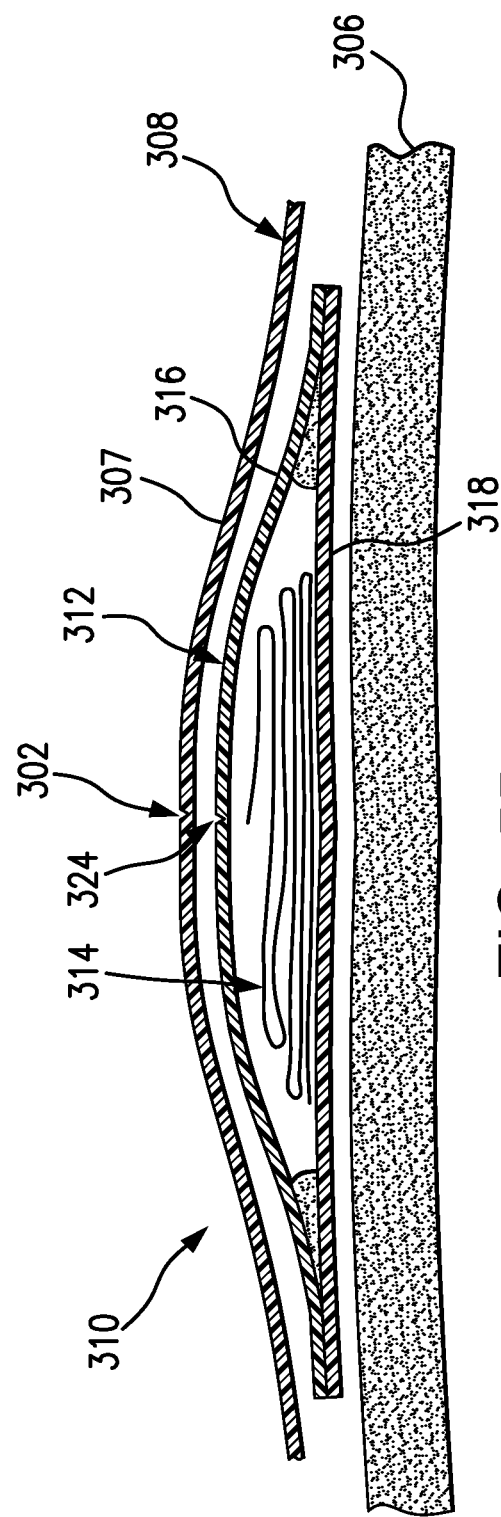
FIG. 55 is a cross-sectional view of a self-contained disposal-bag system according to a fourth example embodiment of the present invention, with the pre-assembled disposal-bag system inserted between two sheets of the diaper.
Figure 56:
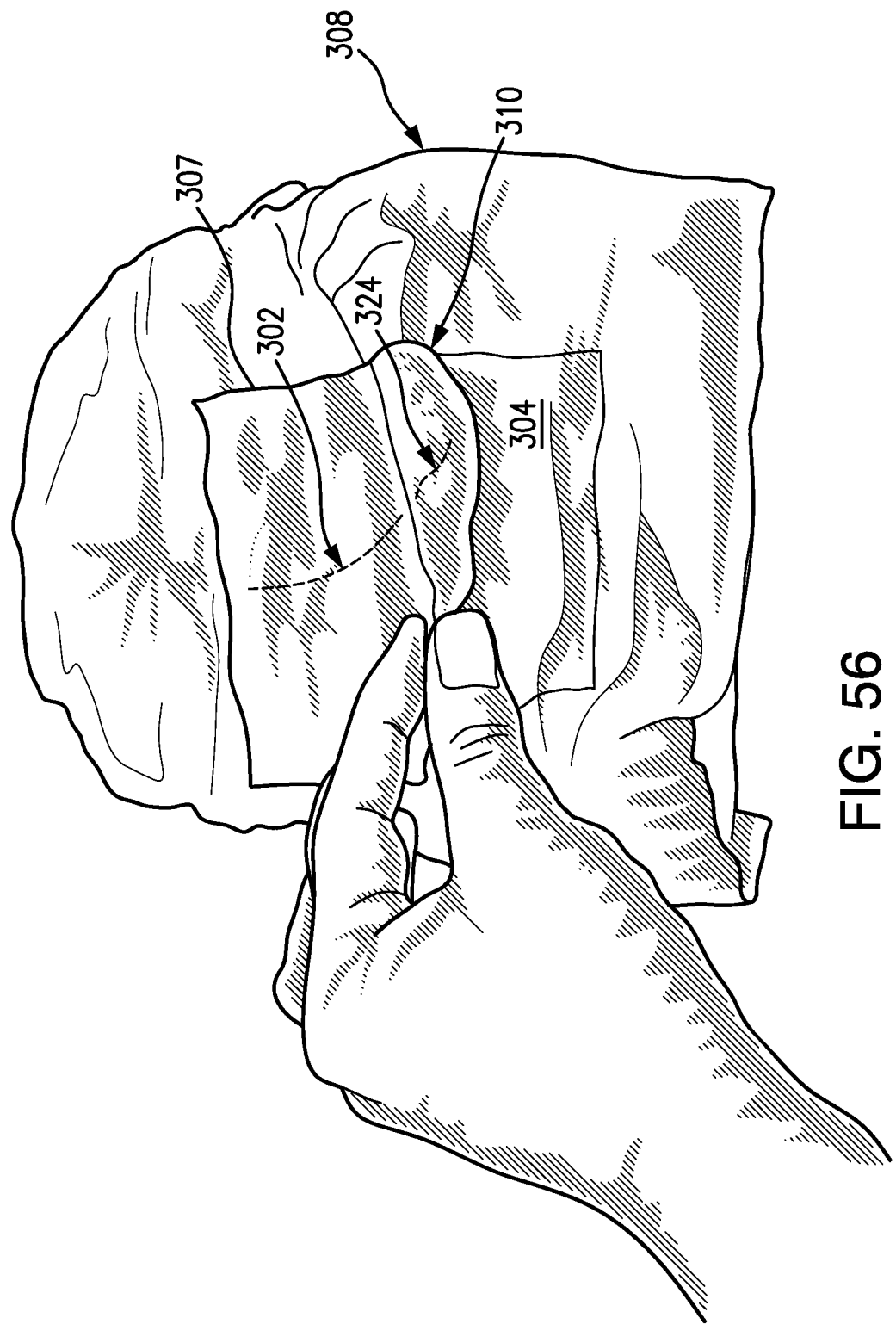
FIG. 56 is a perspective view of the disposal-bag system and diaper of FIG. 55, showing the pre-assembled self-contained disposal-bag system being positioned between two sheets of the diaper.

FIGS. 55-56 show a self-contained disposal-bag system 310 according to a fourth example embodiment of the present invention. This embodiment is similar to those described above, in that it includes a container 312 and a disposal bag 314 stored within the container and extendible from the container through an openable closure 324, with the container 312 including top and bottom sheets 316 and 316. In this embodiment, however, the pre-assembled system 310 is positioned between the diaper backing 307 and an internal sheet 306 of the diaper 308. The backing 307 includes an openable closure 302 that is aligned with the container closure 324 so that the bag 314 can be extended through both aligned closures.

Figure 57:
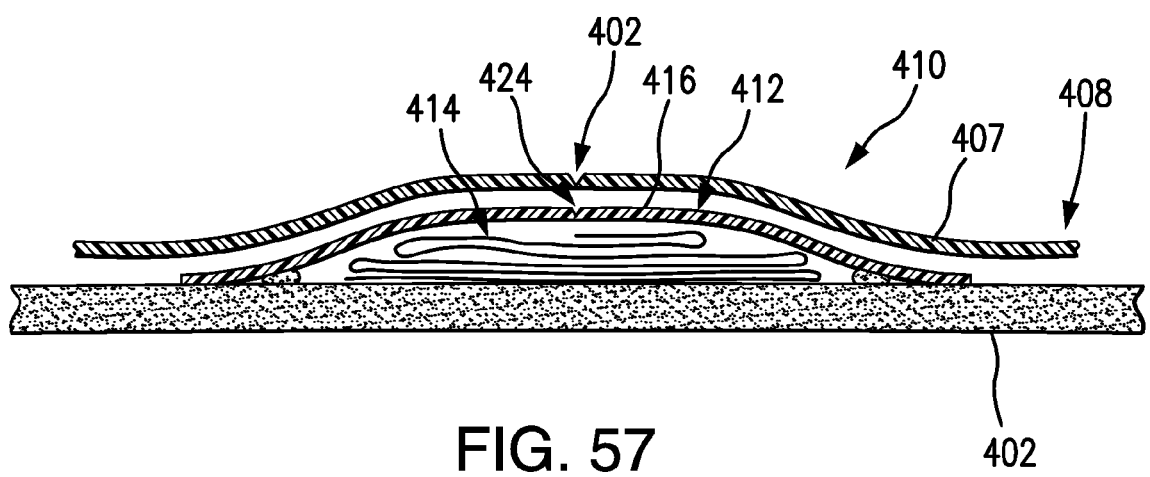
FIG. 57 is a cross-sectional view of a self-contained disposal-bag system according to a fifth example embodiment of the present invention, with the bottom sheet of the container defined by an internal sheet of the diaper.
Figure 58:
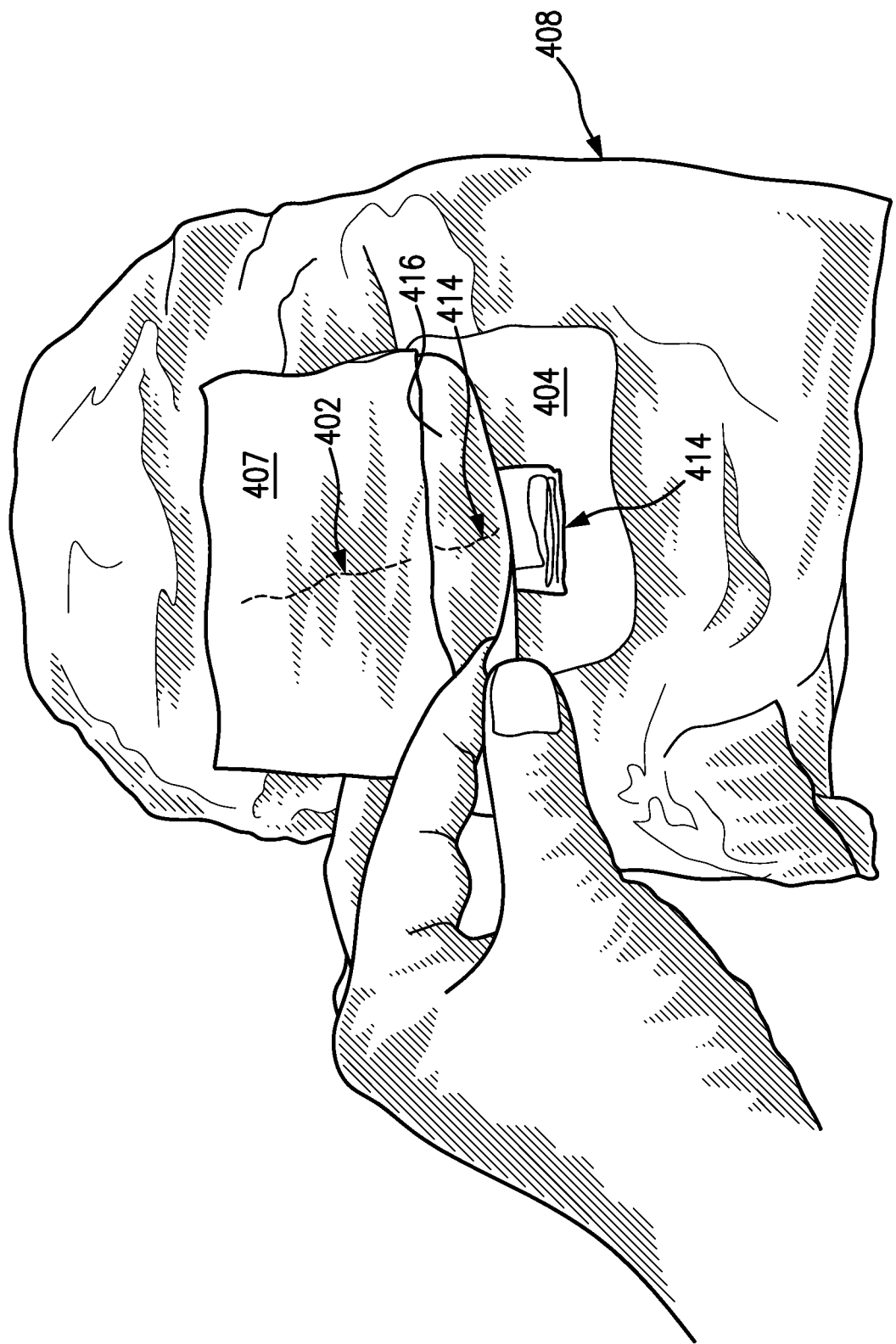
FIG. 58 is a perspective view of the disposal-bag system and diaper of FIG. 57, showing the bag and top sheet of the self-contained disposal-bag system positioned between two sheets of the diaper.

FIGS. 57-58 show a self-contained disposal-bag system 410 according to a fifth example embodiment of the present invention. This embodiment is similar to those described above, in that it includes a container 412 and a disposal bag 414 stored within the container and extendible from the container through an openable closure 424. In this embodiment, however, the bottom sheet of the container 412 is defined by an internal layer 404 of the diaper 408. And the diaper backing 407 includes an openable closure 402 that is aligned with the container closure 424 so that the bag 414 can be extended through both aligned closures. To make the system 410, the bag 414 can be attached to diaper internal sheet 304 (which in this case is also the container bottom sheet), the top sheet 416 attached to the internal sheet, and then the backing 407 attached to the internal sheet.

Figure 59:
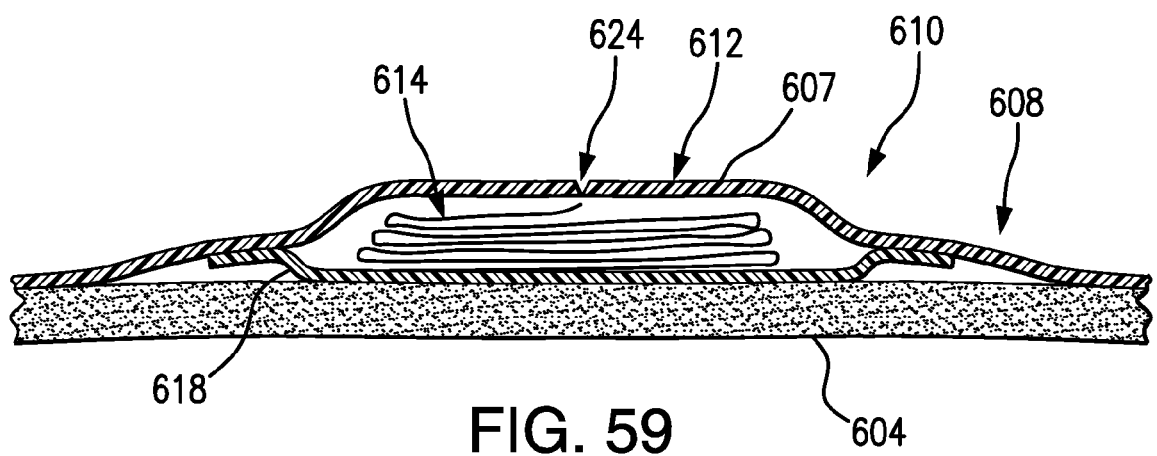
FIG. 59 is a cross-sectional view of a self-contained disposal-bag system according to a sixth example embodiment of the present invention, with the top sheet of the container defined by an outer sheet of the diaper.

FIG. 59 shows a self-contained disposal-bag system 510 according to a sixth example embodiment of the present invention. This embodiment is similar to those described above, in that it includes a container 612 and a disposal bag 614 stored within the container and extendible from the container through an openable closure 624. In this embodiment, however, the top sheet of the container 612 is defined by the backing 607 (the outer sheet) of the diaper 608. To make the system 610, the bag 614 can be attached to the container bottom sheet 618, the diaper backing 607 (which in this case is also the container top sheet) attached to the backing, and the backing attached to an internal layer 604 of the diaper 608.

Figure 60:
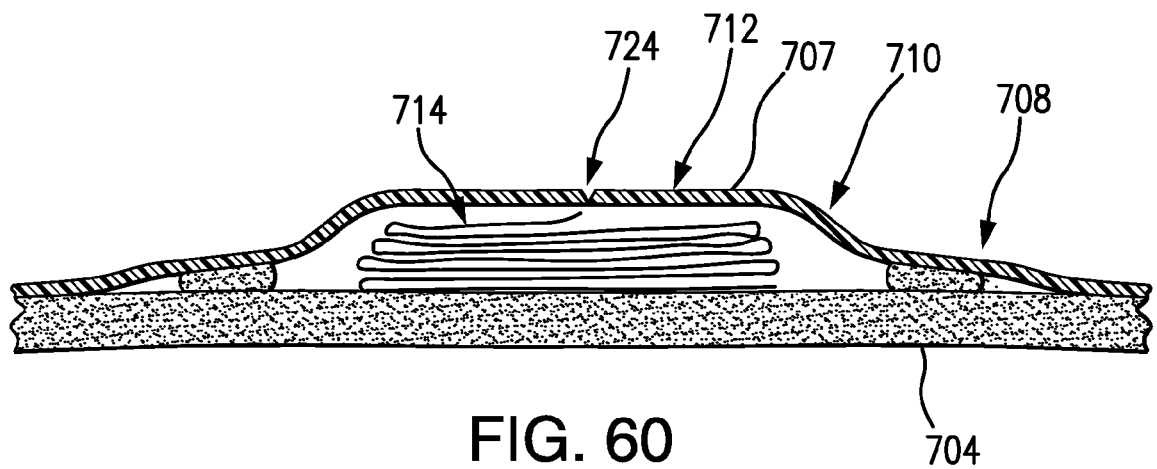
FIG. 60 is a cross-sectional view of a self-contained disposal-bag system according to a seventh example embodiment of the present invention, with the top sheet of the container defined by an outer sheet of the diaper and the bottom sheet of the container defined by an internal sheet of the diaper.

And FIGS. 60-61 show a self-contained disposal-bag system 710 according to a seventh example embodiment of the present invention. This embodiment is similar to those described above, in that it includes a container 712 and a disposal bag 714 stored within the container and extendible from the container through an openable closure 724. In this embodiment, however, the top and bottom sheets of the container 712 are defined by the backing 707 (the outer sheet) and an internal sheet 706 of the diaper 708, respectively, with the container closure 724 formed in the diaper backing. Thus, the container 712 is formed by two sheets of the diaper 708, thereby minimizing the thickness of the assembled system 710 and diaper. To make the system 710, the bag 714 is attached to the diaper internal sheet 706 (which in this case is also the container bottom sheet) and then the backing 707 (which in this case is also the container top sheet) is attached to the internal sheet.

In other embodiments, the disposal-bag system is attached to or formed at least partially by other objects that are worn by humans (or other animals) for absorption of bodily fluids, such as feminine hygiene products (e.g., sanitary pads, napkins, and liners) and other objects such as medical-waste products (e.g., wound dressings, compression garments, and surgical-tray liners). In these embodiments, the disposal-bag systems can be modified as would be readily understood by persons of ordinary skill in the art. For example, in sanitary napkin applications, the container can be sized smaller (width and thickness) and elongated and rectangular-shaped (to generally confirm to the shape of the napkin), the container closure can be located at one end of the container, and the bag can be sized smaller and folded over lengthwise only once with its bottom attachment end and its top pulling end adjacent the closure at that same end. In this way, the thickness of the overall system is minimized for comfort and discretion, while still providing a large-enough bag for disposal of the napkin.

Accordingly, the disposal-bag systems of the present invention provide a number of advantages over the prior art. The disposal-bag systems can be embodied in age-specific designs that maximize safety and utility. The disposal-bag systems efficiently contain the mess of changing a soiled diaper while eliminating the escape of offensive odors and inhibiting the spread of bacteria and germs. When using the diaper disposal-bag systems, soiled diapers are sealed within a sanitary waste bag that can be safely discarded in any trash container or stored anywhere for later disposal. The disposal-bag system is effectively an extension of existing diaper product lines and can easily be added to any standard disposable diaper during the manufacturing process. And all materials used in the construction of the disposal-bag systems can be completely biodegradable.

In addition, the bags used in the disposal-bag systems can be made to have a pleasant scent and can be fabricated from super-lightweight synthetic materials that are flexible, are impervious to liquids, and form a barrier to offensive odors. This is an advantage over using conventional grocery bags and shopping bags that are very thin and usually contain small holes on the bottom. The holes found in conventional shopping bags require double bagging of the soiled diapers to keep liquids and odors contained. The disposal bags of the disposal-bag systems have sufficient volume and flexibility to also be useful for containing used baby wipes and other small waste materials. For example, used baby wipes can be rolled within the soiled diaper prior to enclosing it in the disposal bag. And the disposal bags of the disposal-bag systems can be sized so that, after the soiled diaper is enclosed in the bag, there remains excess room in the bag to add additional waste items if necessary.

Furthermore, depending on the current location where a baby needs changing, conventional bags may not be in reach. When using a disposable diaper with the disposal-bag system, the disposal bag is always there and available. Dirty diapers can be sealed in the disposal bag for later disposal and in the meantime be stored for convenience, for example while at home (eliminating the need for expensive DIAPER GENIE diaper containers), changing a baby on the road (for example, in the back of the car, at the beach, on an airplane, camping, at a restaurant, visiting friends and relatives, at sporting events, etc.).

Moreover, the visible top sheet of the disposal-bag system can be made of the same or a similar material as conventional disposable diapers, so the appearance of the top sheet can be made with a pattern, texture, etc., to match or blend in with that of the diaper. The disposal-bag systems can be engineered with multiple safeguards for the protection of children. And using the disposal-bag systems contributes to a more odor-free trash receptacle and makes the entire diaper-changing experience more pleasant. In sum, the disposal-bag systems improve the diaper-changing experience of parents and caregivers by providing a more convenient, sanitary, and odor-free disposal system and method.

It is to be understood that this invention is not limited to the specific devices, methods, conditions, or parameters described and/or shown herein, and that the terminology used herein is for the purpose of describing particular embodiments by way of example only. Thus, the terminology is intended to be broadly construed and is not intended to be unnecessarily limiting of the claimed invention. For example, as used in the specification including the appended claims, the singular forms "a," "an," and "one" include the plural, the term "or" means "and/or," and reference to a particular numerical value includes at least that particular value, unless the context clearly dictates otherwise. In addition, any methods described herein are not intended to be limited to the sequence of steps described but can be carried out in other sequences, unless expressly stated otherwise herein.

While the invention has been shown and described in example forms, it will be apparent to those skilled in the art that many modifications, additions, and deletions can be made therein without departing from the spirit and scope of the invention as defined by the following claims.

What is claimed is:

1. A disposal-bag system for an object, comprising:
    a pod container attached to an object, having a bottom sheet and a top sheet attached together and defining an internal cavity, and having an open-able closure manipulable from a closed state to an opened state;

the top sheet includes a permeable top layer, a bottom layer, and an intermediate bonding agent layer for bonding the permeable top layer of the topsheet and the bottom layer of the top sheet together;

the bottom sheet includes an intermediate layer, a top bonding agent ring layer for joining the intermediate layer of the bottom sheet and the bottom layer of the top sheet along their peripheries, and a bottom bonding agent layer for joining the pod container to the object; and a folded bag is positioned between the top sheet and bottom sheet and is attached to the bottom sheet, extendible from the pod container through an opening of the openable closure, such that upon opening the openable closure, the bag can be extended from the pod container, opened, and inverted to place the object therein without detaching the folded bag from the pod container.

2. The disposal-bag system of claim 1, wherein the bag stored in the pod container is folded flat into a compact arrangement.

3. The disposal-bag system of claim 2, wherein the folded I bag includes an impermanent bond releasably connecting free side edges of the bag together to retain the bag in the folded arrangement, wherein in use the impermanent bond can be broken, by adult finger strength and dexterity, to release the free side edges from each other to unfold the bag, wherein the impermanent bond does not retain the bag open top in a closed state.

4. The disposal-bag system of claim 1, wherein the bag includes an at least partially removable pull tab at the top open end, wherein the pull tab retains the top end in a closed state, and wherein the pull tab is positioned adjacent the closure of the pod for access upon opening the closure and when pulled, it will separate the top and bottom layer of the pod.

5. The disposal-bag system of claim 1, wherein the top sheet includes the openable closure having an elongated failure zone that when caused to fail, forms the opening.

6. The disposal-bag system of claim 5, wherein the elongated failure zone in the closed state includes no overlapping layers.

7. The disposal-bag system of claim 6, wherein the elongated failure zone in the opened state is not returnable to the closed state.

8. The disposal-bag system of claim 1, wherein the openable closure includes a releasable attachment assembly with a peripheral stitching and a pull-string arranged such that when the pull-string is pulled the stitching releases the top sheet from the bottom sheet, wherein the openable closure extends all the way across the top sheet such that when the openable closure is manipulated to the open state the top sheet separates into two pieces, and wherein the top sheet pieces are attached to the bag.

9. The disposal-bag system of claim 1, wherein the object is a diaper, a feminine-hygiene product, or a medical-waste dressing or garment.

10. A method of disposing of a disposable object, comprising:
 providing the disposal-bag system of claim 1;
 attaching the bag system to the disposable object;
 opening the openable closure of the pod container;
 pulling a top end of the bag through the opening with a bottom end of the bag remaining attached to and within the pod container;
 opening the bag;
 grasping the disposable object;
 inverting the bag so that the disposable object is now positioned within the inverted bag; and
 closing the bag with the disposable object positioned therein.

11. The method of claim 10, wherein the step of opening the openable closure of the pod container includes applying a force to cause a failure zone in the pod container to fail and thereby form the opening through which the bag top can be extended.

12. The method of claim 10, wherein the step of opening the openable closure of the pod container includes applying a force to cause a failure zone in the pod container to fail and thereby form an opening extending all the way across the top sheet of the pod container, accessing a pull-string through the opening, pulling the pull-string to release stitching connecting the top sheet and a bottom sheet of the pod container until the top sheet separates from the bottom sheet and the top sheet separates into two pieces that are attached to the bag.

13. The method of claim 10, wherein the step of opening the bag includes releasing an impermanent bond releasably connecting free edges of the bag together to retain the bag in a folded arrangement.

14. The method of claim 10, wherein the step of opening the bag includes at least partially removing a pull tab at the top end of the bag that retains the bag top end in a closed state.

15. The method of claim 10, wherein the disposable object is a diaper, a feminine-hygiene product, or a medical-waste dressing or garment.

* * * * *